United States Patent [19]
Williamson, IV et al.

[11] Patent Number: 5,817,093
[45] Date of Patent: Oct. 6, 1998

[54] IMPEDANCE FEEDBACK MONITOR WITH QUERY ELECTRODE FOR ELECTROSURGICAL INSTRUMENT

[75] Inventors: Warren P. Williamson, IV, Loveland; David C. Yates, West Chester, both of Ohio

[73] Assignee: Ethicon Endo-Surgery, Inc., Cincinnati, Ohio

[21] Appl. No.: 743,321

[22] Filed: Nov. 4, 1996

Related U.S. Application Data

[63] Continuation of Ser. No. 362,070, Dec. 22, 1994, abandoned, which is a continuation-in-part of Ser. No. 311,297, Sep. 23, 1994, Pat. No. 5,558,671, which is a continuation-in-part of Ser. No. 95,797, Jul. 22, 1993, Pat. No. 5,403,312.

[51] Int. Cl.⁶ .................................................. A61B 17/36
[52] U.S. Cl. ............................. 606/50; 606/51; 606/42; 606/46
[58] Field of Search ........................... 606/27–34, 37–42, 606/45–52; 607/100–102; 128/642

[56] References Cited

U.S. PATENT DOCUMENTS

| | | |
|---|---|---|
| 2,031,682 | 2/1936 | Wappler et al. . |
| 4,608,981 | 9/1986 | Rothfuss et al. . |
| 4,633,874 | 1/1987 | Chow et al. . |
| 4,651,280 | 3/1987 | Chang et al. . |
| 4,655,216 | 4/1987 | Tischer . |
| 4,671,274 | 6/1987 | Sorochenko . |
| 4,685,459 | 8/1987 | Koch et al. . |
| 4,985,030 | 1/1991 | Melzer et al. ............................. 606/51 |
| 5,057,107 | 10/1991 | Parins et al. ............................. 606/48 |
| 5,085,659 | 2/1992 | Rydell ...................................... 606/47 |

(List continued on next page.)

FOREIGN PATENT DOCUMENTS

| | | |
|---|---|---|
| 0 517 244 | 12/1992 | European Pat. Off. . |
| 0 518 230 | 12/1992 | European Pat. Off. . |
| A-0 552 050 | 1/1993 | European Pat. Off. . |
| A-0 556 705 | 2/1993 | European Pat. Off. . |
| A-0 558 317 | 2/1993 | European Pat. Off. . |
| A-0 640 317 | 7/1994 | European Pat. Off. . |
| A-38 30 193 | 3/1990 | Germany . |

(List continued on next page.)

OTHER PUBLICATIONS

Automatically Controlled Bipolar Electrocoagulation—"COA–COMP", Neurosurg. Ref. (1984) 187–190; B. Vallofors and B. Bergdahl.

Radio Frequency Energy and Impedance Feedback, SPIE vol. 1068 Catheter–Based Sensing and Imaging Technology (1989).

Instrument for Stomach Resection and Bowel Anastomosis Used During Closed Procedures, Department of Surgery of Mukachevo City Hospital, N.G. Vittenberger, Jan.–Feb. 1958, First Issue (the 211th).

*Primary Examiner*—Michael Peffley

[57] ABSTRACT

Query electrodes are provided for monitoring the electrical impedance of tissue as it is treated with electrosurgical energy. In one embodiment, based on a predicted model of tissue impedance and a number of initial impedance readings, the impedance at which tissue treatment is completed is predicted. More particularly, a minimum impedance level is measured and a function of the minimum impedance is used to determine impedance at which coagulation is completed. A control device is provided for bringing the output of the generator within an optimum range based on a system load curve. In one embodiment the impedance monitoring device is used in conjunction with a bipolar electrosurgical instrument. Preferably, the instrument comprises electrically opposite therapeutic electrodes, each located on one or more tissue engaging surfaces for engaging tissue to be treated, and electrically opposite query electrodes, located on one or more tissue engaging surfaces. The therapeutic electrodes provide therapeutic energy to the tissue while the query electrodes provide a lower voltage electrical sensing energy for the purpose of measuring tissue impedance at various stages, e.g. before, during, or after tissue treatment.

41 Claims, 15 Drawing Sheets

U.S. PATENT DOCUMENTS

| | | |
|---|---|---|
| 5,104,025 | 4/1992 | Main et al. . |
| 5,151,102 | 9/1992 | Kamiyama et al. ......................... 606/51 |
| 5,167,658 | 12/1992 | Ensslin ....................................... 606/34 |
| 5,190,517 | 3/1993 | Zieve et al. ................................. 604/22 |
| 5,201,900 | 4/1993 | Nardella ................................... 606/157 |
| 5,207,691 | 5/1993 | Nardella ................................... 606/142 |
| 5,300,070 | 4/1994 | Gentelia et al. ........................... 606/45 |
| 5,307,976 | 5/1994 | Olson et al. . |
| 5,389,098 | 2/1995 | Tsuruta et al. . |
| 5,403,312 | 4/1995 | Yates et al. . |
| 5,417,687 | 5/1995 | Nardella et al. ........................... 606/32 |
| 5,423,809 | 6/1995 | Klicek ....................................... 606/38 |
| 5,429,636 | 7/1995 | Shikhman et al. ........................ 606/41 |
| 5,443,463 | 8/1995 | Stern et al. ................................. 606/51 |
| 5,496,312 | 3/1996 | Klicek ....................................... 606/34 |

FOREIGN PATENT DOCUMENTS

| | | |
|---|---|---|
| 39 42 998 A1 | 7/1991 | Germany . |
| 2 213 381 | 8/1989 | United Kingdom . |
| WO 93/08754 | 5/1993 | WIPO . |
| WO-A-93 08757 | 5/1993 | WIPO . |
| WO 93/13718 | 7/1993 | WIPO . |
| WO 94/24949 | 11/1994 | WIPO . |
| WO 94/24951 | 11/1994 | WIPO . |
| WO-A-94 24949 | 11/1994 | WIPO . |

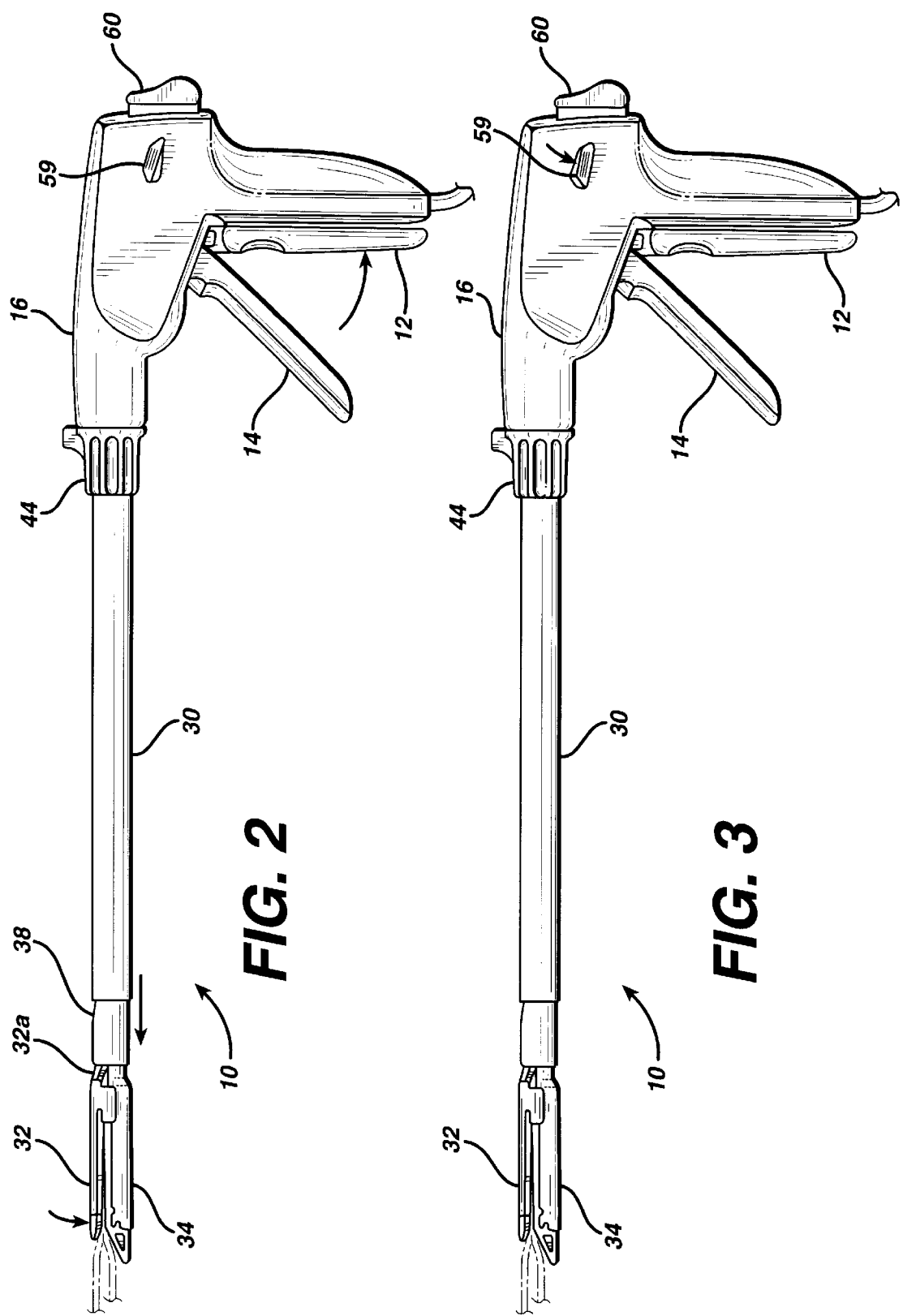

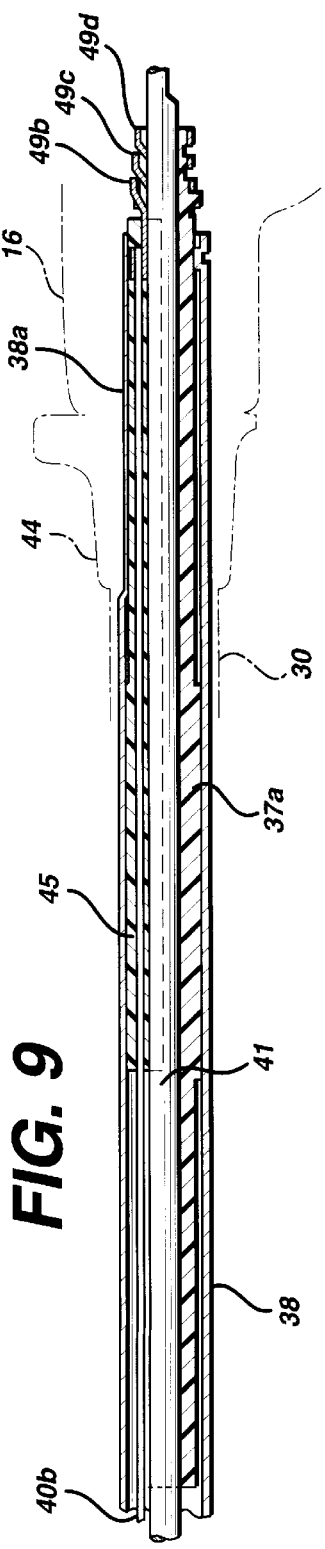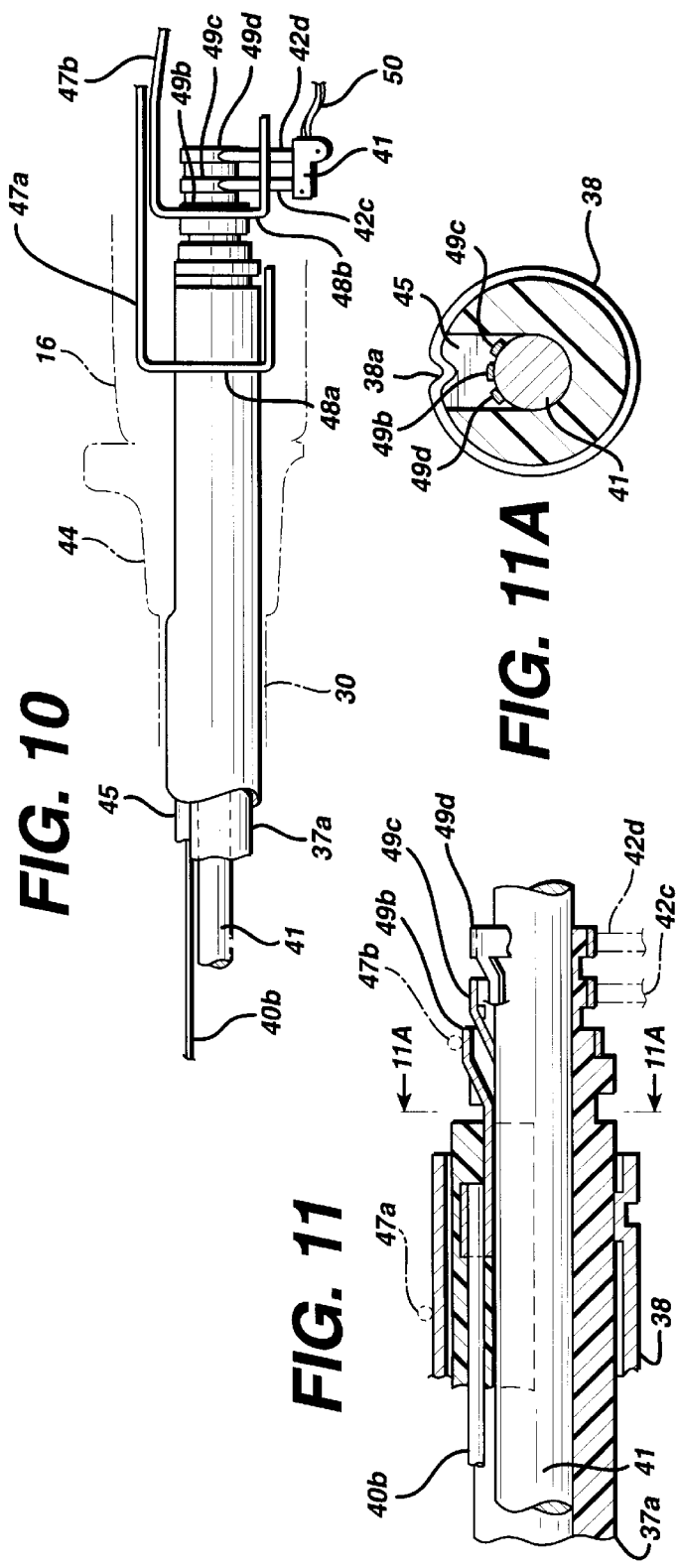

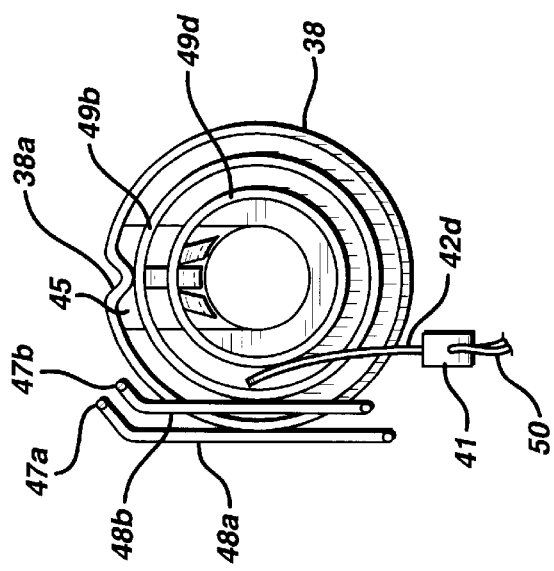
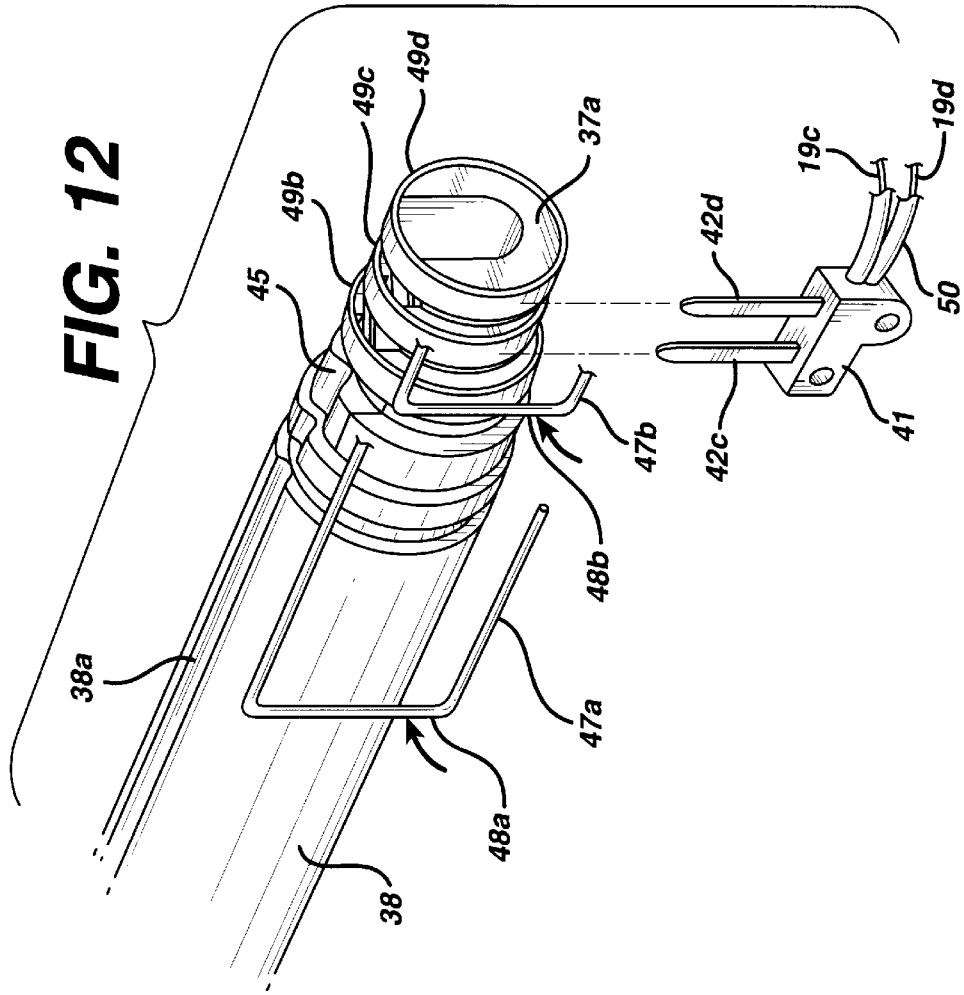

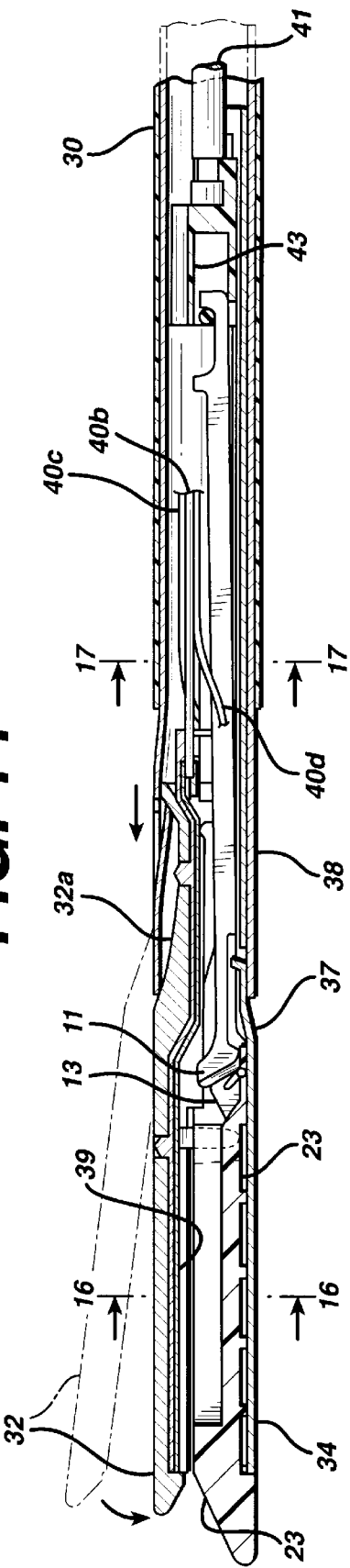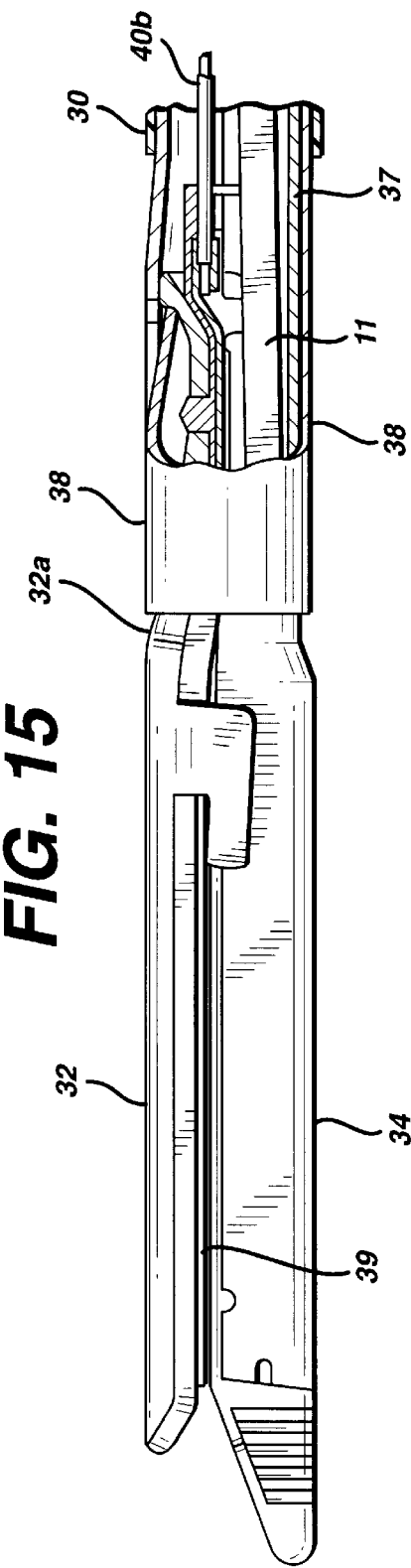

IMPEDANCE FEEDBACK MONITOR WITH QUERY ELECTRODE FOR ELECTROSURGICAL INSTRUMENT

This is a continuation, of application Ser. No. 08/362, 070, filed Dec. 22, 1994 (now abandoned) which is a continuation-in-part of application Ser. No. 08/311,297 filed Sep. 23, 1994 and issued as U.S. Pat. No. 5,558,671, which is a continuation of application Ser. No. 08/095,797 filed Jul. 22, 1993 and issued as U.S. Pat. No. 5,403,312.

FIELD OF THE INVENTION

This invention relates to electrosurgical tissue treatment, and in particular, to a method and apparatus for controlling the electrosurgical treatment of tissue by measuring impedance of the tissue being treated by an electrosurgical device.

BACKGROUND OF THE INVENTION

Electrosurgical instruments are used for example, for cutting, coagulation, tissue welding, ablation, and dissection. Electrosurgical generators are used to supply therapeutic electrosurgical energy in the radio frequency (RF) range to such instruments. Usually such generators include controls that regulate the voltage and/or current so that a select power level range is delivered and a maximum power level is not exceeded.

When such electrosurgical instruments are used, the primary control is the experience of the surgeon who responds to what is observed to be happening to the tissue as it is treated with the RF energy. Often, particularly for endoscopic procedures, surgeons cannot readily see what is happening to the tissue. Also, the change in tissue properties due to the RF energy may occur very quickly. As a result, some problems which may occur include tissue charring, sticking of tissue to the electrodes of the surgical instrument, thermal spread, and over or under treatment of tissue.

It has been recognized that the tissue impedance changes as RF energy is applied to the tissue. Attempts have been made to control the power delivered to the tissue as the tissue impedance changes. For example, tissue impedance has been used to maintain constant power or voltage levels. Also tissue impedance, specifically the differential quotient of tissue impedance as RF power is applied, has been used to determine an initial power level and to switch off RF power when the differential quotient of impedance reaches a preset value.

Notwithstanding these control arrangements, there is a continuing need for improvement in the control of electrosurgical energy deliverance to the tissue and/or determination of when tissue treatment has reached an optimal level.

In particular there is a need to provide a device and method for measuring impedance and impedance changes in tissue to determine tissue characteristics, particularly to determine the end point of coagulation for a variety or a range of tissue impedances.

SUMMARY OF THE INVENTION

The present invention provides an electrosurgical device which includes query electrodes for measuring one or more electrical parameters of tissue prior to, during, or after treating the tissue with therapeutic electrodes. These measured tissue parameters may be used to determine various tissue characteristics, such as, for example, tissue type, tissue impedance characteristics, status of tissue treatment, completion of tissue coagulation, etc. One aspect of the present invention provides a signal indicating the measured tissue characteristic. In one embodiment, a control signal is provided for controlling the delivery of electrosurgical energy in response to the measured tissue characteristic. The control signal may completely shut off RF energy or otherwise adjust the level, frequency, etc. of the energy delivered to the tissue through the therapeutic electrodes.

In a preferred embodiment, the query electrodes are used to measure tissue impedance. However, various other electrical parameters may be measured or used to determine tissue characteristics.

In one embodiment, the present invention provides an impedance monitoring device and/or method which monitors the impedance of tissue located between electrically opposite query electrodes associated with (i.e., located at, located on, coupled to, layered on, adhered to, etc.) tissue contacting surfaces of an end effector of a therapeutic electrosurgical instrument. The instrument further comprises electrically opposite therapeutic electrodes associated with the end effector. The therapeutic electrodes are adapted to deliver therapeutic electrosurgical energy to treat tissue in contact therewith.

In accordance with the present invention, a tissue impedance monitor is provided which continuously or periodically measures tissue impedance, preferably as electrical energy is delivered to tissue. The present invention provides for a determination, based on tissue impedance, of tissue characteristics prior to, during or after being treated with electrosurgical energy. In a preferred embodiment, based on a model of expected tissue impedance behavior over time as electrosurgical energy is delivered to tissue, the monitored tissue impedance is used to determine tissue status. This will be described in more detail below. A signal indicating status of tissue is provided either to a user or to an instrument controller. The device may also include a switch which automatically turns off the electrical energy when treatment is completed.

According to known tissue impedance models, tissue impedance initially drops as electrical energy is applied and then begins to rise again as coagulation occurs. Based on this known tissue behavior, in a preferred embodiment of the present invention, a point is selected where tissue treatment is to be completed. Tissue impedance is monitored by the query electrodes located at selected strategic positions on the end effector until this event occurs.

In one embodiment, a value for the minimum impedance is established, i.e., when the impedance is at its lowest value as the energy is applied. Then, the impedance value anticipated to provide the desired tissue effect is determined by calculating a selected function of the established minimum impedance. When the measured impedance rises to the level of the impedance value for the desired result, e.g., coagulation, tissue welding or a level of diathermy, the instrument will indicate or provide a response for such event. The present invention is preferably adapted so that the condition is detected for a range of expected tissue impedances which varies according to tissue type, area and/or volume.

In a preferred embodiment the desired tissue condition is where coagulation is completed. When this point has been reached a feedback signal is provided to a control unit or to the user, at which time the energy supply is switched off. The feedback signal may, for example, control a visual, audible or tactile signal to a user, and/or may provide instructions to a control unit to automatically turn off energy supplied to the tissue.

In accordance with one aspect of the present invention, an electrosurgical apparatus for coagulating tissue during a surgical procedure is provided comprising an end effector including first and second elements movable relative to one another for engaging tissue to be coagulated therebetween. Each of the first and second elements comprises an opposing tissue contacting surface. At least one of the first and second elements includes a first therapeutic electrode associated on one of the electrically opposite therapeutic poles. The first therapeutic electrode is arranged to be in contact with the tissue engaged to be coagulated. The query electrodes comprise at least one query electrode corresponding to a first pole and at least one query electrode corresponding to an electrically opposite second pole. Preferably, when tissue is engaged, both query electrodes are in contact with tissue to be coagulated. The query electrodes are preferably arranged to measure impedance at strategic locations depending on the desired information. For example, the electrodes may be placed on the periphery of the interfacing or opposing tissue engaging surfaces. A power controller responsive to a power control signal provides RF energy to the tissue contacting electrode(s) of the first and/or second elements.

Impedance measuring circuitry is coupled to the electrical circuit which delivers energy to the query electrodes. The impedance measurement circuitry measures the impedance of the tissue between query electrodes. Feedback circuitry providing a control signal to the generator to control output to the therapeutic electrodes is coupled to the impedance measuring circuitry.

In a preferred embodiment the control signal to the generator controls output to the therapeutic electrodes based on a function of the measured impedance value(s). The feedback circuitry includes a first device for determining a minimum impedance value and holding said minimum impedance value. A second device provides a threshold determining circuit coupled to the first device. The threshold determining circuit determines a threshold impedance value as a function of the held minimum impedance value.

The threshold determining circuit may comprise an analog device for determining the function of minimum impedance or a digital circuit including, for example, a look up table for determining the threshold impedance value based on an input minimum impedance value.

After a threshold value has been determined, a first comparator compares the measured impedance value to threshold impedance value and generates a power control signal to the power controller to control the therapeutic RF energy delivered to the tissue upon the condition of the measured impedance value exceeding the threshold impedance value.

A power controller may include at least one electrical switch for selectively supplying RF energy to the instrument to coagulate tissue positioned between the first and second elements.

The power controller may selectively switch off the power supplied to the tissue under a number of conditions, for example, when the measured impedance value exceeds the threshold impedance value.

Although the instrument may be a monopolar device or a multipolar device (i.e. including two or more therapeutic electrodes providing energy in waveforms as measured from any pole to any other pole as having a phasic relationship), the end effector preferably includes two electrically opposite therapeutic electrodes corresponding to two electrically opposite therapeutic poles.

In the preferred bipolar device, each query and therapeutic electrode is located on either one or both of the opposing tissue contacting surfaces. Each of the first and second electrically opposite query electrodes comprises one or more tissue contacting query electrodes and each of the first and second therapeutic electrodes comprises one or more tissue contacting therapeutic electrodes. The therapeutic electrodes are arranged on the distal end of the electrosurgical device so that when the first and second elements close together to engage tissue, electrically opposite therapeutic electrodes are located either on the same surface or opposing surfaces between a portion of the engaged tissue.

The query electrodes are arranged on the distal end of the electrosurgical device so that when the first and second elements close together to engage tissue, electrically opposite query electrodes are located either on the same surface or opposing surfaces between a portion of the engaged tissue. An impedance monitoring circuit monitors the impedance of the tissue between the query electrodes as low voltage RF energy is delivered through the query electrodes to the tissue. Preferably, the frequency of RF energy delivered through the query electrodes is different from the frequency of energy delivered through the therapeutic electrodes to reduce electrical interference.

In one preferred embodiment each of the therapeutic electrodes corresponding to a first pole are offset with respect to the interfacing surface from each of the therapeutic electrodes corresponding to the second pole. In other words, the therapeutic electrodes are offset from each other so that they are not diametrically opposed from each other on interfacing surfaces or they are separated and insulated from each other on the same surface.

In a preferred embodiment the electrosurgical instrument compresses tissue in a compression zone between the first interfacing surface and the second interfacing surface and applies therapeutic electrical energy through the compression zone. More preferably, the compression zone is an area defined by a compression ridge on one of the interfacing surfaces which compresses the tissue against the other interfacing surface. Alternatively or in addition, there may be a compression ridge on both interfacing surfaces. The query electrodes may be located laterally outside of the compression zone, within the compression zone, spaced adjacent to the compression zone, distally or proximally on the end effector, etc. depending upon the intended application of the instrument.

One embodiment includes a cutting element associated with an end effector. The cutting element is arranged to cut tissue at or near the coagulation site. Preferably, the coagulation is completed prior to any mechanical or other cutting at or around the coagulation site. The query electrodes are thus arranged so that the impedance sensor can determine when coagulation or cauterization has occurred at the cutting site. The cutting element then may be used to cut through the coagulated tissue or between two zones of tissue coagulation.

In another embodiment, therapeutic and query electrodes are incorporated into a linear cutter similar to a linear cutting mechanical stapler. In this embodiment the instrument preferably comprises two substantially parallel and elongated therapeutic electrode bars which are associated with one therapeutic pole, and a slot for cutting means to travel between the bars. Optionally one or more rows of staples may be provided on each side of the slot outside of the bars to provide mechanical tissue security or approximation during the healing process.

In operation of a preferred embodiment, tissue is clamped between the two elements of the instrument, and electrical energy in the form of RF energy is supplied to the compressed tissue to coagulate or cauterize tissue along the two substantially parallel bars. Simultaneously, electrical energy, preferably of a lower voltage and a different RF frequency, is supplied to the query electrodes to sense the impedance of the tissue therebetween. Based on the impedance modeling of the device with this specific electrode configuration, an appropriate function of the minimum impedance is incorporated into the impedance feedback circuit to determine an appropriate threshold impedance level. A warning mechanism is used to warn the user when the impedance is out of range or exceeds the threshold impedance level. Also, the warning signal may be directed to a control circuit or power controller adapted to then provide an appropriate generator response, including where appropriate to turn off the RF energy or to adjust the generator output level, frequency, waveform, etc., delivered through therapeutic electrodes.

In accordance with another aspect of the present invention a method of electrosurgically treating tissue during surgical procedure is provided. Accordingly, a preferred method comprises the steps of: applying RF energy to tissue to be electrosurgically treated through one or more tissue query electrodes associated with the end effector of an electrosurgical instrument; measuring the impedance of the tissue between electrically opposite query electrodes associated with the instrument end effector; generating an impedance signal representative of the measured impedance of the tissue; and controlling the RF energy applied to the tissue through the therapeutic electrodes in response to the impedance signal. Preferably the tissue treating electrodes are electrically opposite bipolar electrodes.

The step of controlling the RF energy applied to the tissue through the therapeutic electrodes may comprise the steps of: determining and holding minimum impedance value; determining a threshold impedance value based on a function of the minimum impedance value; comparing measured impedance values to the threshold impedance value; and generating a control signal to control or switch off the power of the controller upon the condition of measured impedance value exceeding the threshold impedance value.

In accordance with yet another aspect of the present invention, a method of electrosurgically treating tissue during a surgical procedure comprises the steps of: providing an electrosurgical instrument having an end effector comprising first and second tissue engaging surfaces, at least one of said first and second tissue engaging surfaces including thereon a tissue contacting therapeutic electrode associated with a first pole of an electrosurgical system and at least one of said first and second tissue engaging surfaces containing thereon a second tissue contacting therapeutic electrode associated with a second pole of the therapeutic system; at least one of said first and second tissue engaging surfaces including thereon a first query electrode associated with a first pole of an impedance sensing system and a second query electrode associated with a second pole of an impedance sensing system; engaging tissue to be coagulated between the first and second tissue engaging surfaces; selectively controlling RF energy supplied to the first and second tissue contacting therapeutic electrodes for coagulating tissue positioned therebetween; measuring the impedance of the treated tissue with said first and second query electrodes; setting a threshold impedance value at which tissue treatment is complete; comparing measured impedance values to the threshold impedance value; and controlling or switching off the RF energy connected to the first and second therapeutic electrodes upon the condition of the measured impedance value reaching or exceeding the threshold impedance value.

Other objects and advantages of the invention will apparent from the following description, the accompanying drawings and the following claims.

BRIEF DESCRIPTION OF THE DRAWINGS

FIG. 2 is a side elevational view of the embodiment of FIG. 1 shown in a closed, clamped position, before cutting or stapling;

FIG. 3 is a side elevational view of the embodiment of FIG. 2 shown as RF energy is applied to tissue;

FIG. 9 is a longitudinal cross-sectional view of the intermediate portion of the instrument;

FIG. 10 is an elevational view of the proximal end of the intermediate portion showing the contact of the wireforms to their respective contact positions;

FIG. 11 is an enlarged cross-sectional view of the proximal end of the intermediate portion of the instrument;

FIG. 11a is a transverse cross sectional view taken along the lines 11a—11a of FIG. 11.

FIG. 12 is a perspective view showing the wireforms contacting their respective contact position;

FIG. 13 is an end view of FIG. 11 showing a slight bias in the wireforms, allowing for pressure of the wireforms onto their respective contact positions;

FIG. 14 is a longitudinal cross-sectional view of the distal end of the instrument of FIG. 1 shown in a closed and clamped position;

FIG. 15 is an enlarged partial cross-sectional view of the distal portion of FIG. 13;

DETAILED DESCRIPTION OF THE INVENTION

While the present invention is generally applicable to a variety of electrosurgical instruments including monopolar, bipolar and multipolar, and both conventional and endoscopic, it will be described herein with reference to an endoscopic bipolar linear cutting and stapling instrument.

Operation of linear cutting and stapling instruments are known in the art and are discussed, for example, in U.S. Pat. Nos. 4,608,981, 4,633,874, and U.S. application Ser. No. 07/917,636 incorporated herein by reference.

The query electrodes are preferably used to determine the impedance of tissue at a given time prior to, during, or after tissue treatment. However other uses are contemplated, such as monitoring delivery of current or voltage, phase shift, and frequency response of tissue.

In one embodiment, an impedance monitoring device using query electrodes determines when the tissue has been treated to a desired degree at a particular location. Preferably this treatment is completed when the tissue has been cauterized and before excessive thermal spread, tissue sticking, burning or charring occurs. The impedance of tissue as it is being heated with electrosurgical energy generally follows a characteristic tissue impedance curve. According to the impedance curve, generally the impedance will decrease, arrive at a minimum value, and then rise as coagulation and tissue desiccation occurs. At an impedance or within a range of impedances on a characteristic curve, coagulation will predictably occur.

Figure 21:
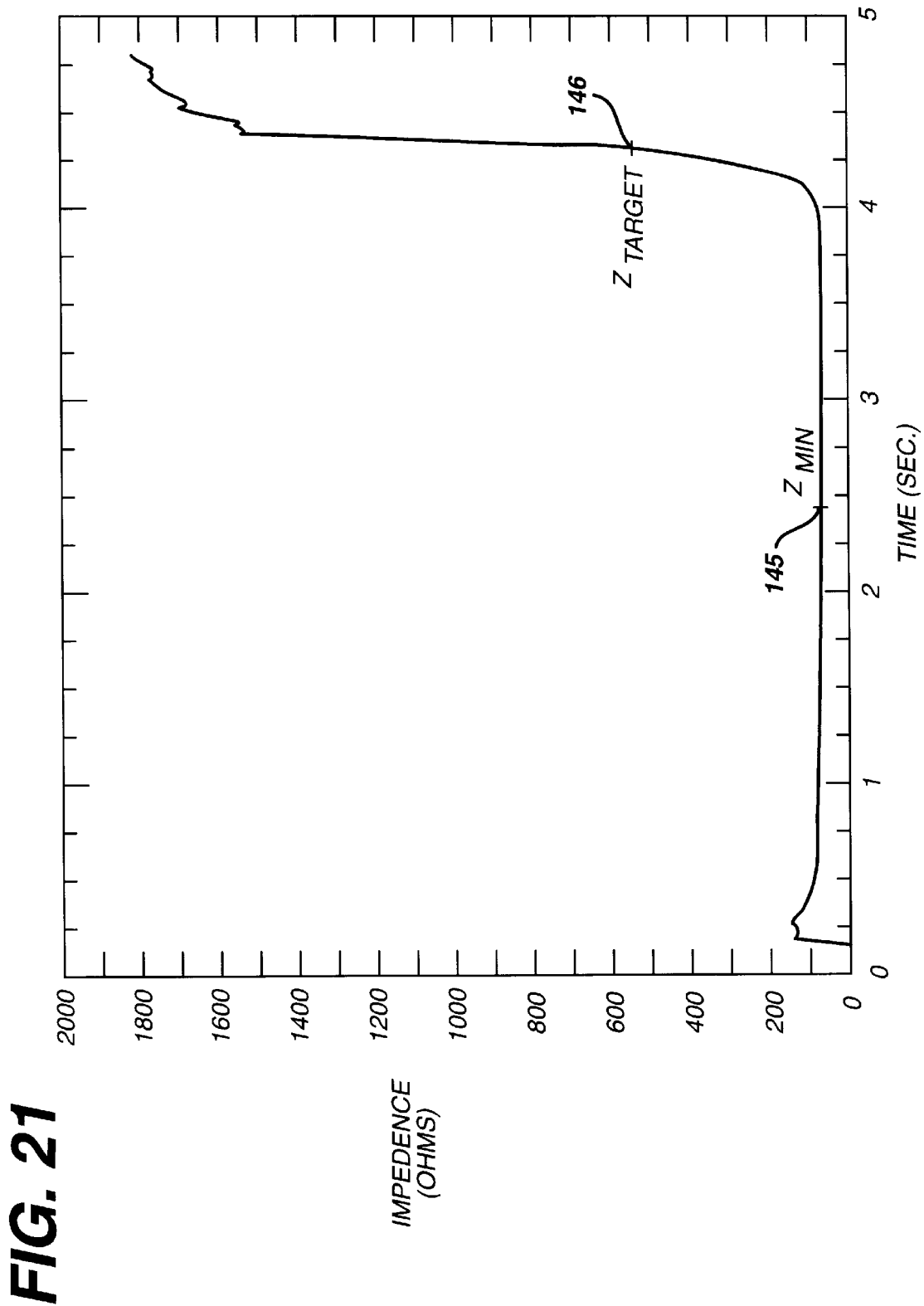
FIG. 21 is a characteristic curve illustrating the change in impedance over time during application of electrosurgical energy to tissue using the electrosurgical instrument illustrated in FIG. 1.

FIG. 21 is a characteristic impedance curve illustrating the change in tissue impedance over time, during the application of electrosurgical energy using the electrosurgical instruments illustrated in FIGS. 1–19. The present invention determines a threshold impedance on the curve at which coagulation has occurred, $Z_{target}$ 146. This impedance is based on the value of the lowest impedance on the curve, $Z_{min}$ 145, i.e., when the impedance has stopped falling and begins to rise. A function of the minimum impedance $f(Z_{min})$ is used to approximately predict a point at which coagulation occurs, $Z_{target}$ 146.

Referring now to FIGS. 1–17 there is illustrated an instrument of the present invention to be used in conjunction with an impedance feedback device. An endoscopic linear cutting and stapling instrument 10 is shown having a housing 16 coupled to a sheath 30 with a lumen extending therethrough and an end effector 15 extending from the distal end of the sheath 30. The end effector 15 comprises first and second elements which are comprised of interfacing jaw members 32, 34. Jaw member 32 is movably secured to jaw member 34. The housing 16 has a clamping trigger 12 for closing jaw members 32, 34, an RF switch detente arm 58 and electrical switch contacts 67a, 67b, coupled to an electrical switch 59 for turning on RF energy, and a firing trigger 14 for advancing the cutting element 11 through tissue and and wedge 13 for applying staples 17. Jaw members 32, 34 are shown in an unclamped position in FIG. 1; in a clamped position prior to application of electrosurgical energy and prior to cutting and stapling in FIG. 2; in a clamped position after application of electrosurgical energy and prior to cutting and stapling in FIG. 3; and in a clamped position after cutting and stapling in FIG. 4.

Figure 1:
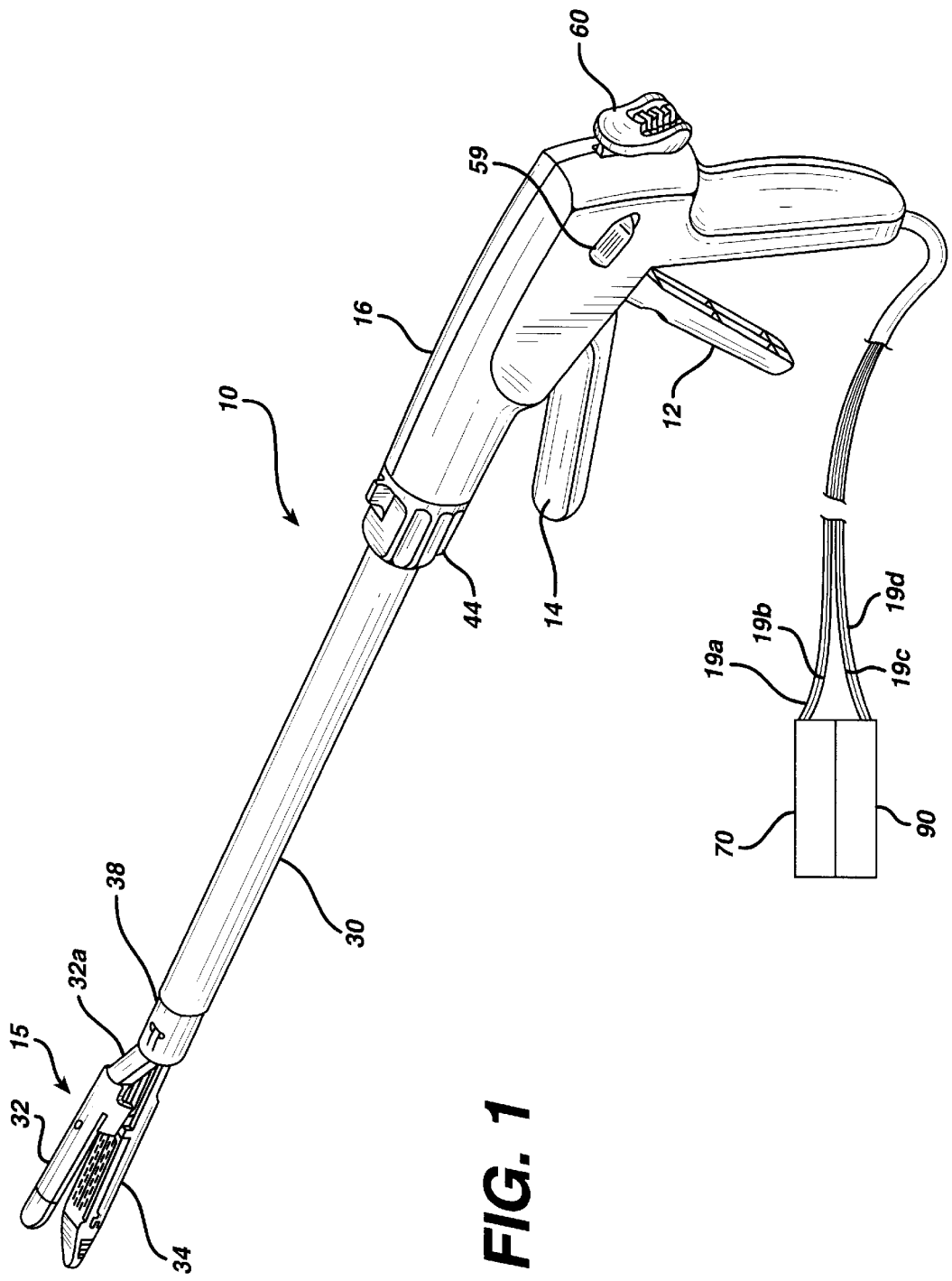
FIG. 1 is a perspective view of an endoscopic electrosurgical instrument one embodiment of the present invention.
Figure 4:
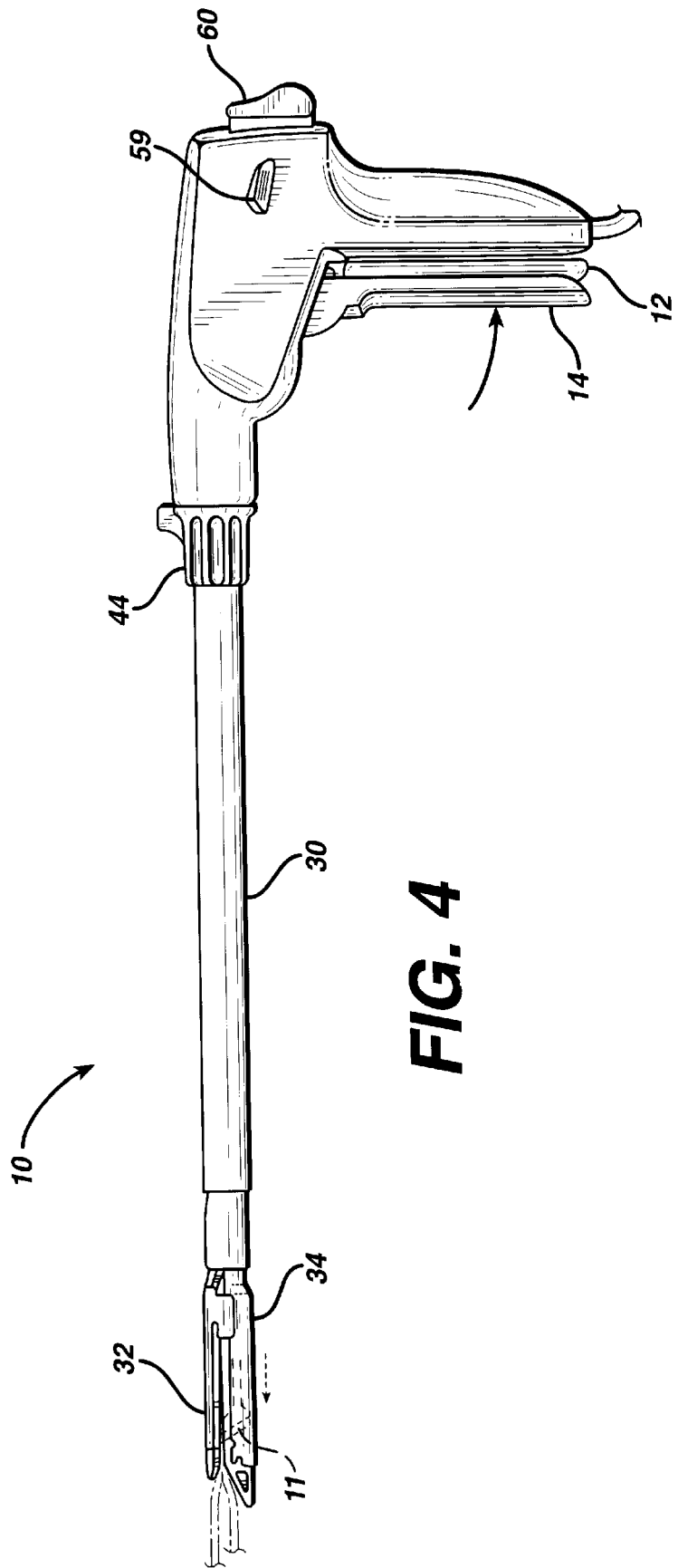
FIG. 4 is a side elevational view similar to FIG. 3 shown after RF energy has been applied and the tissue has been stapled and cut.
Figure 5:
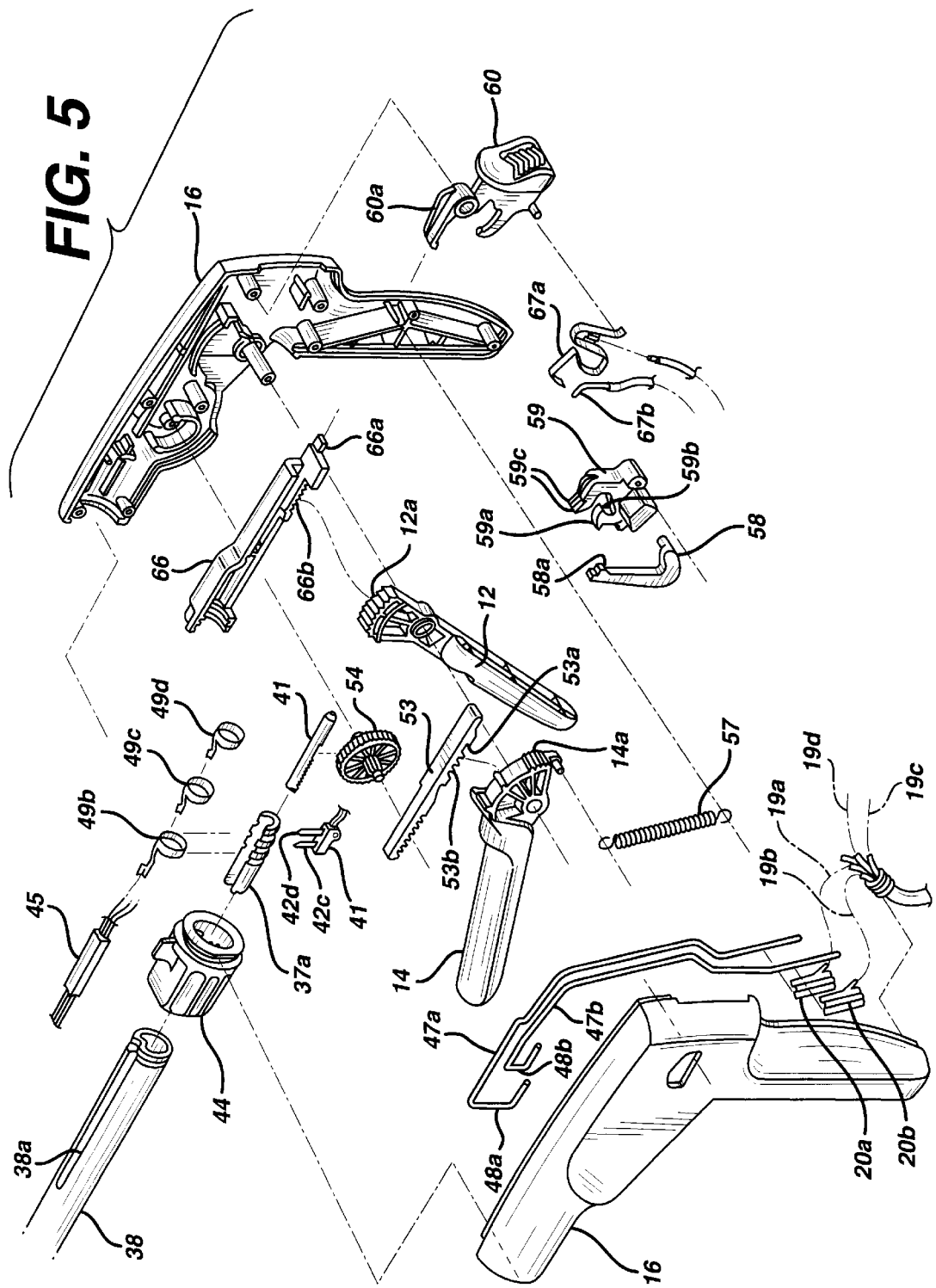
FIG. 5 is an exploded perspective view of the proximal handle portion of the instrument of FIG. 1.
Figure 6:
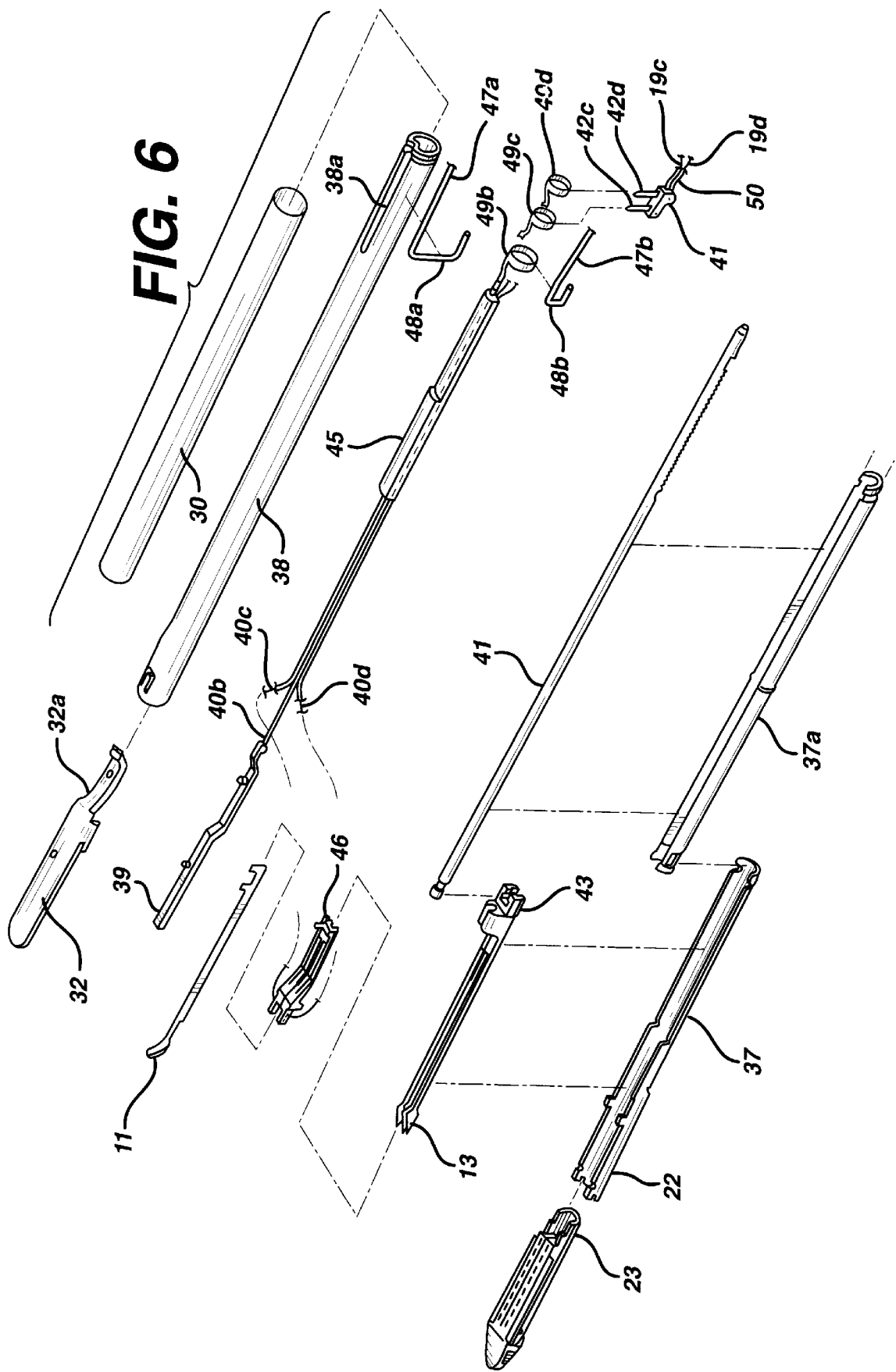
FIG. 6.is an exploded perspective view of the intermediate and distal portion of the instrument of FIG. 1.
Figure 7:
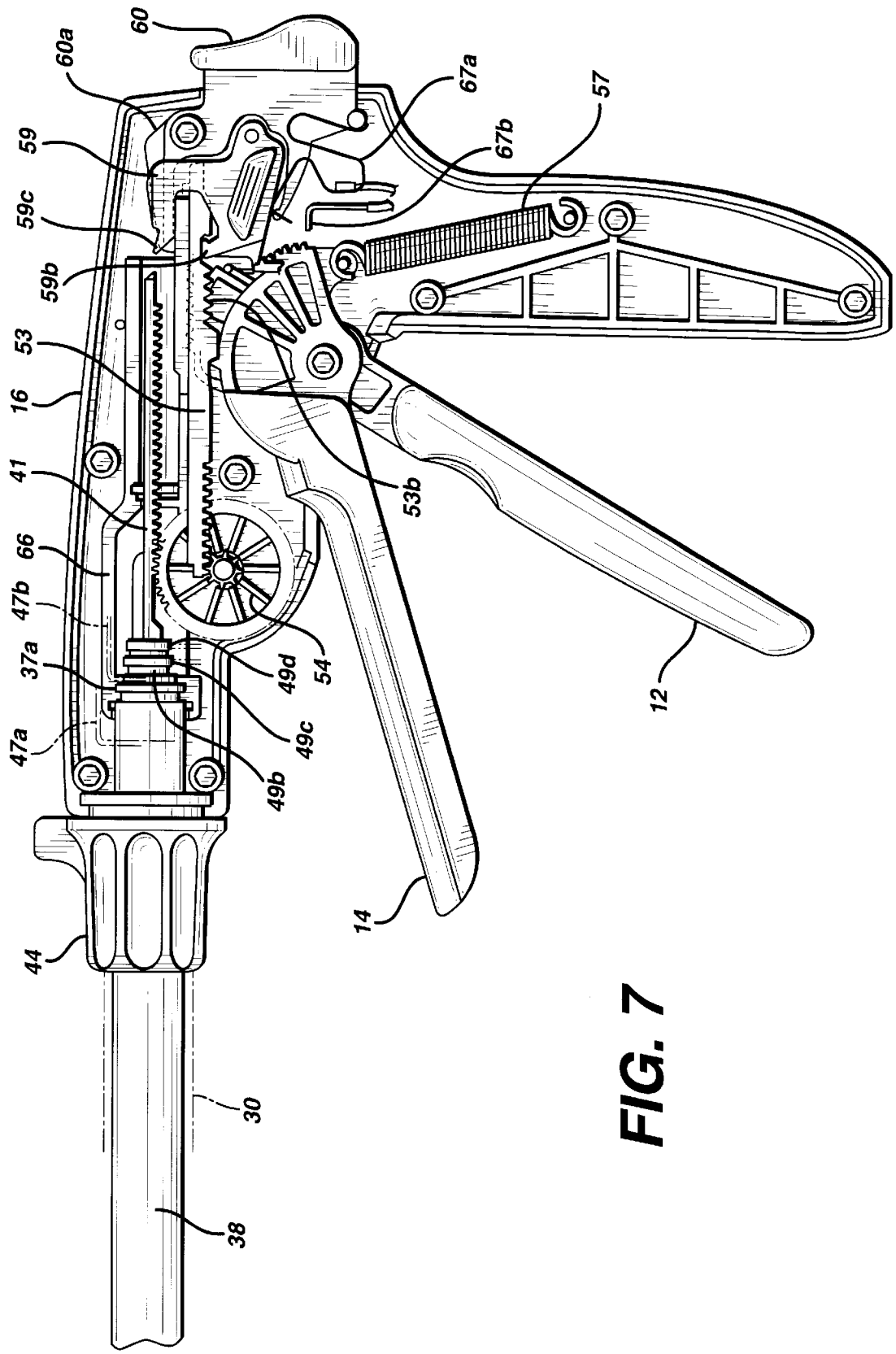
FIG. 7 is a side elevational view of the proximal handle portion in a first, open position of the instrument of FIG. 1, shown with the left side handle cover and wireforms removed.
Figure 8:
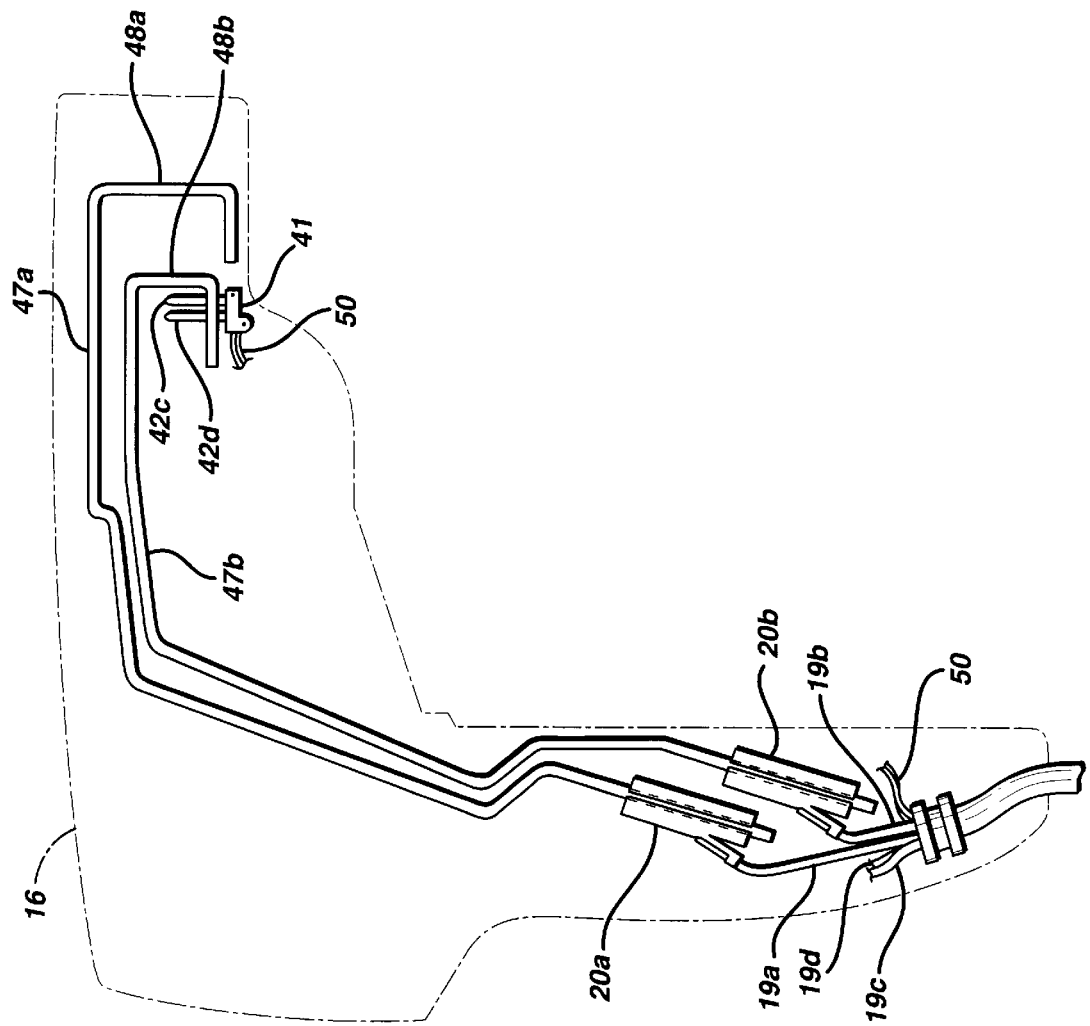
FIG. 8 is an elevational view of the inside of the left side handle portion showing the location of the wireforms and connectors used in the present invention.
Figure 16:
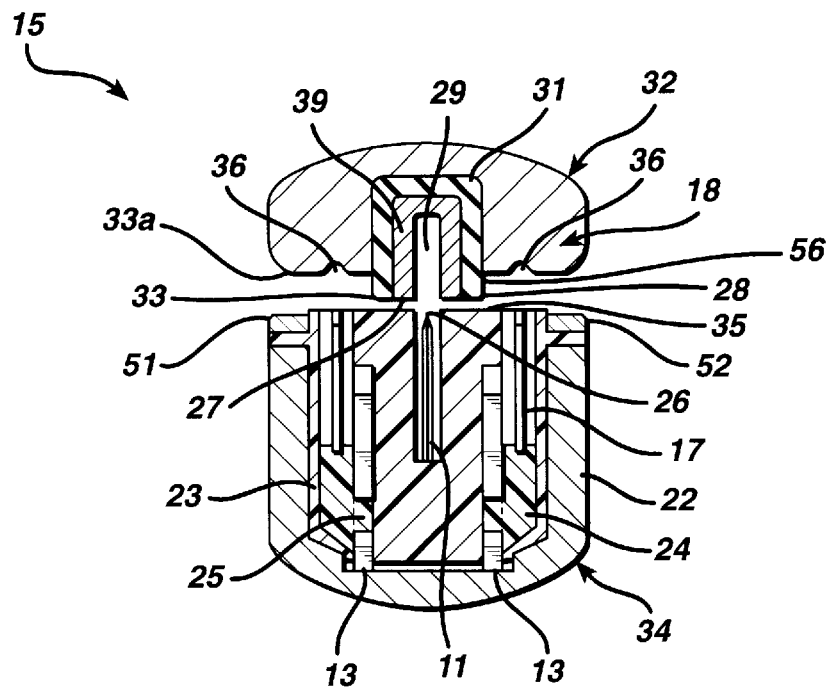
FIG. 16 is a transverse cross-sectional view taken along line 16—16 of FIG. 14.
Figure 17:
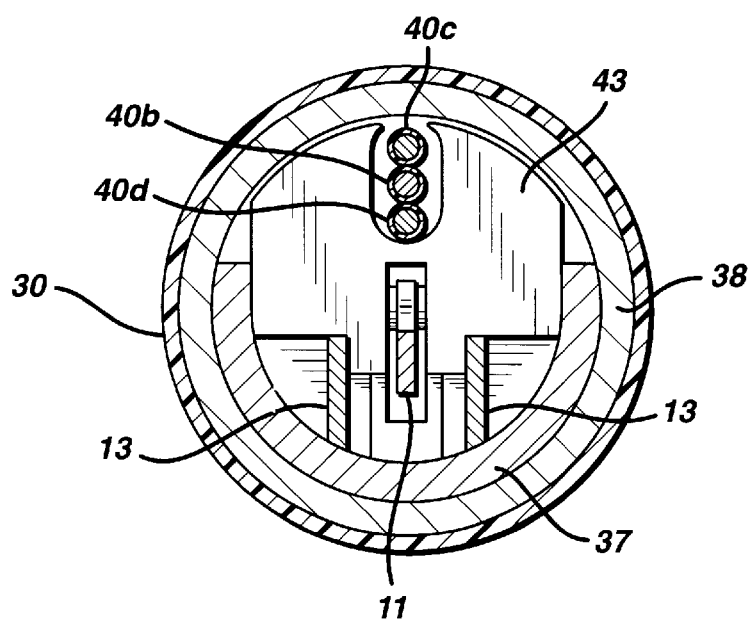
FIG. 17 is a transverse cross-sectional view taken along line 17—17 of FIG. 14.

Jaw member 32 comprises an anvil 18, U-shaped therapeutic electrode 39 extending along the length of the jaw 32, and a U-shaped insulating material 31 surrounding the outside of the therapeutic electrode 39. Jaw member 32 has an inner surface 33 which substantially faces an inner surface 35 of jaw member 34. The U-shaped electrode 39 comprises two electrically communicating electrode bars 27, 28 forming a first pole and located on and extending substantially along the length of the inner surface 33. The U-shaped electrode 39 is comprised of a conductor, such as, aluminum or surgical grade stainless steel. The bars 27, 28 are separated by a knife channel 29 extending longitudinally through the middle of the electrode 39. Pockets 36 located on anvil 18 for receiving staple ends are located along the inner surface 33, along the length and outside of bars 27, 28, to form a row of staples on each side of electrode 39. The electrode bars 27, 28 and insulating material 31 form a ridge 56 extending out relative to an anvil portion 33a of the inner surface 33 (FIG. 16). The electrode 39 acts as a first pole of a bipolar tissue treatment or therapeutic system. The anvil 18 is formed of an electrically conductive material and acts as a second therapeutic electrode of the bipolar treatment or therapeutic system, the anvil being electrically opposite of the treatment electrode 39. The anvil 18 is electrically isolated from electrode 39 by the U-shaped insulating material 31.

Jaw member 34 comprises a cartridge channel 22 and a cartridge 23 releasably inserted into the cartridge channel 22. The cartridge 23 includes a track 25 for wedge 13, a knife channel 26 extending longitudinally through the center of the cartridge 23, a series of drivers 24 extending into the track 25 and staples 17 arranged in two sets of single rows.

Jaw member 34 further comprises a first query electrode 51 located on the cartridge 23 and separated from cartridge channel 22, by an insulating material and a second query electrode 52 located on the cartridge channel 22 on the opposite lateral side of a plane defined by the knife channel 27 as the first query electrode 51 and separated from the cartridge channel 22 by an insulating material. The query electrodes 51, 52 are located towards the lateral side periphery of the surface 35 so that tissue impedance across an entire engaged tissue section will be measured. The query electrodes 51, 52 are also recessed from the plane defined by the cartridge 23 so that the query electrode 51, 52 will not contact the anvil 18 when the jaws 32, 34 are closed.

The sheath 30 is formed of an insulative material and has an electrically conductive closure tube 38 extending through its lumen. In a preferred embodiment, the closure tube 38 acts as a jaw closure tube and as an electrical contact. A channel retainer 37a extends from the proximal end of the closure tube 38 and is secured to channel 37 which there extends distally through the remainder of the closure tube 38 to form jaw member 34. The channel 37 includes cartridge channel 22 extending distally from the closure tube 38.

The body 16 has a clamping trigger 12 for advancing the closure tube 38 to close the jaws 32, 34 towards each other engaging tissue therebetween. Rotation of the clamping trigger 12 causes the closure tube 38 to advance co-axially through the sheath 30 over a camming surface 32a of jaw 32 to close the jaws 32, 34 onto tissue situated between the jaws 32, 34.

The channel retainer 37a guides co-axial movement of a drive rod 41 within the channel 37. The drive rod 41 is advanced by the rotation of the firing trigger 14 as described in more detail below. The driving rod 41 is coupled on its distal end to a block 43. The block 43 is coupled to a cutting means 11 and a staple driving wedge 13, which the drive rod 41 advances by way of the block 43 into the end effector 15. A wedge guide 46 is used to guide wedge 13 into track 25. Jaw member 32 is secured by way of the channel 37 to the jaw member 34.

When the drive rod 41 advances the cutting element 11, the cutting element 11 advances through the knife channel 26 in between the bars 27, 28 to cut tissue engaged by jaws 32, 34 when the tissue has been cauterized. Thus, the cut line is medial to the coagulation lines formed by the bar electrodes 27, 28. The drive rod 41 simultaneously advances the block 43 and thus the wedge 13 which drives the drivers 24 into the staples 17 causing the staples 17 to fire through tissue and into the pockets 36 of the anvil 18. Staples 17 are applied in single longitudinal rows on each side of the cutting element 11 as the cutting element 11 cuts the tissue.

A knob 44 located on the distal end of the body 16 rotates the closure tube 38, channel retainer 37a, channel 37 and end effector 15 which are directly or indirectly coupled to the knob 44 so that the knob 44 may be used for rotational placement of the end effector jaws 32, 34. The knob 44 includes a peg (not shown) which fits into and engages indentation 38a closure tube 38. Closure tube 38 is fitted at its proximal end, into the housing 16.

Electrical energy is supplied to the electrode 39, anvil 18, first query electrode(s) 51, 151 or 251 and second query electrode(s) 52 or 252 from electrosurgical generators 70, 90 (FIG. 20) through connections such as those described below, or other connections means, such as, for example, like those described in parent application Ser. No. 08/095, 797, incorporated herein by reference. The generators 70, 90 are user controlled by way of RF switch 59 located in the housing 16.

Wires 19a, 19b, 19c and 19d extend into the body 16 of the instrument and deliver energy to electrodes 39, 18, 51, 52, respectively. Wires 19a, 19b are coupled to low impedance contact elements 20a, 20b respectively and contact elements 20a, 20b are coupled to wireforms 47a, 47b respectively. Wireforms 47a, 47b are exposed at their distal ends 48a, 48b. Wireforms 47a and 47b are biased respectively towards closure tube 38 and contact ring 49b located on the proximal end of channel retainer 37a, so as to make electrical contact with the closure tube 38 and ring 49b respectively. Wires 19c, 19d extend into housing 16 in the form of ribbon wire 50. Ribbon wire 50 is coupled to a contact block 41, having contact fingers 42c, 42d. The contact block 41 is secured to the housing 16. Wire 19c is in electrical contact with finger 42c and wire 19d is in electrical contact with finger 42d. Finger 42c and finger 42d are biased towards contact rings 49c and 49d respectively, located on the proximal end of the channel retainer 37a, so as to make electrical contact with rings 49c, 49d respectively.

Wire 19a delivers electrical current to the anvil 18 by way of first wire form 47a which contacts electrically conductive closure tube 38 which contacts electrically conductive anvil 18 as closure tube 38 closes jaws 32, 34.

Wire 19b delivers electrical current to the electrode 39 through second wire form 47b which contacts contact ring 49b coupled to wire 40b extending through the closure tube 38 to the electrode 39.

Wire 19c delivers current to the first query electrode 51 through ribbon wire 50 and is coupled to first spring contact finger 42c of a contact block 41. The spring contact finger 42c is biased towards contact ring 49c making electrical contact with contact ring 49c. The electrical contact ring 49c is coupled to wire 40c extending through the closure tube 38 to electrode 51.

Wire 19d delivers current to second query electrode 52 through wire 50 and is coupled to second spring contact finger 42d of a contact block 41. The spring contact finger 42d is biased towards contact ring 49d making electrical contact with contact ring 49d. The electrical contact ring 49d is coupled to wire 40d extending through the closure tube 38 to electrode 52.

The closure tube 38 and ring contacts, 49b, 49c, and 49d, permit the knob 44 to rotate while contact is maintained between closure tube 38, rings 49b, 49c, 49d and wireforms 47a, 47b and spring fingers 42c, 42d, respectively. The rings 49b, 49c, 49d are electrically insulated from each other and from the closure tube 38.

Wires 40a–d extend through seal 45 which fits into channel retainer 37a, which fits into closure tube 38.

Clamping trigger 12 includes gear teeth 12a which movably engage with teeth 66b of yoke 66. Yoke 66 is coupled on its distal end to the closure tube 38. When clamping trigger 12 is actuated, the gear teeth 12a engage with teeth 66b in yoke 66 causing the yoke 66 to advance distally. Closure tube 38 closes jaws 32, 34 as it advances over camming surface 32a of jaw 32.

The RF switch 59 is rotated switch on RF energy to be supplied to the therapeutic and query electrodes. When the RF switch 59 is rotated, detente protrusion 59a on the switch 59 hooks under detente protrusion 58a on detente arm 58, preventing the switch 59 from deactivating RF energy unless the RF switch 59 is manually rotated back to its original position. The RF energy may also be turned off electrically as described herein.

Switch 59 has a moveable contact 67a and a stationary contact 67b. The moveable contact 67a rotates with switch 59 to contact stationary contact 67b when switch is on.

Ledge 60a of release button 60 is engaged with the proximal end of the yoke 66 adjacent step ledge 66a on proximal end of yoke 66. When the yoke 66 is advanced by the clamping trigger 12, the ledge 60a rotates down behind proximal end of yoke 66, thereby preventing yoke 66 from retracting until release button 60 has been pressed. Thus the jaws 32, 34 will remain is a closed position until a user releases the jaws 32, 34 with release button 60.

The switch 59 includes fingers 59c which sit just above proximal end of yoke 66. The ledge 60a of the release button 60 fits in between fingers 59c. The RF switch 59 cannot be activated, i.e., rotated forward, until the yoke 66 has been advanced distally so that fingers 59c of switch 59 are free to rotate behind proximal end of yoke 66.

The switch 59 also includes a lower hook 59b which engages groove 53a of firing rack 53. Firing rack 53 includes gear teeth 53b which are engaged by gear teeth 14a of firing trigger 15. The firing rack 53 is coupled on its distal end to pinion gear 54 which in turn engages the drive rod 41.

When the firing trigger 14 is pulled, the fire rack 53 is advanced distally to rotate pinion 54 which advances the driving rod 41 distally to actuate the cutting element 11 and to drive staples 17 into tissue engaged by the end effector 15.

The firing rack 53 cannot advance however until the lower hook 59b of the RF switch is disengaged from the groove 53a of the firing rack 53. This occurs only when the RF switch 59 has been activated.

Thus, the presently described device includes a lockout device or devices for preventing application of RF energy, staples or knife actuation until the jaws 32, 34 have been closed. The lockout device(s) require the proper sequence is followed as illustrated in FIGS. 1–4, i.e, jaw closure, followed by application of RF energy, followed by staple application and cutting element actuation. It also provides a detented RF switch so that RF energy is continuously applied until the switch 59 is manually released or until the RF energy is switched off by a feedback control signal to the generators 70, 90.

The closure trigger 12 and firing trigger 14 are interlocked and a spring 57 is mechanically coupled to both triggers 12, 14.

When tissue is engaged between clamped jaw members 32, 34, and RF energy has been applied, the firing trigger 14 located on housing 16 may be actuated to advance a cutting element 11 through the engaged tissue to cut the tissue. Simultaneously, when the firing trigger 14 is actuated, the wedge 13 is advanced through the track 25 causing the drivers to 24 to displace towards the staples 17, thereby driving the staples 17 through tissue and into anvil pockets 36.

Figure 18:
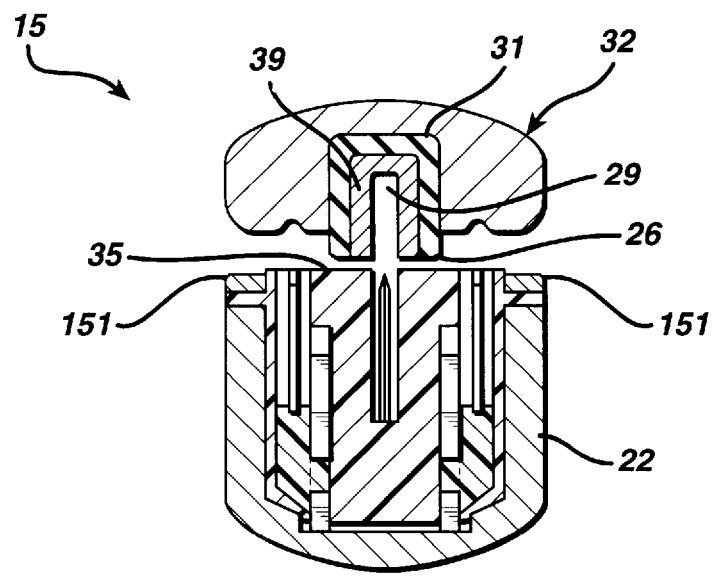
FIG. 18 illustrates a front cross-sectional view of the distal end of an instrument of an alternative embodiment of the present invention.

FIG. 18 illustrates an end effector of an alternative embodiment of the present invention. The end effector is the same as that described with respect to FIG. 16 except for the placement of the query electrodes. The first query electrode, comprises a pair of electrodes 151, located on the cartridge channel 22 on opposite sides of the knife channel 26 and towards the side periphery of surface 35. The second query electrode and the second therapeutic electrode are the same and are comprised of the anvil 18.

Figure 19:
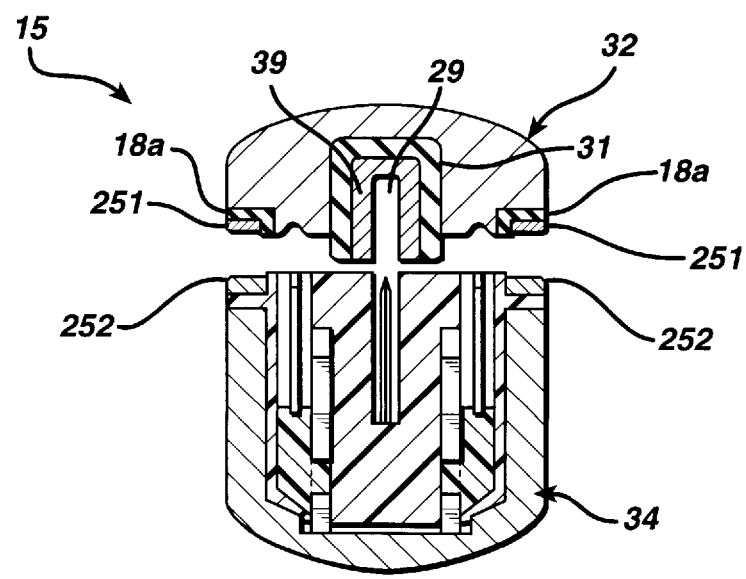
FIG. 19 illustrates a front cross-sectional view of the distal end of an alternative embodiment of the present invention.

FIG. 19 illustrates an end effector of an alternative embodiment of the present invention. The first query electrode comprises a pair of electrodes 251 located on the anvil 18 and electrically isolated from the anvil 18 with an insulating material 18a. The first query electrodes 251 are located on opposite sides of the knife channel 29 from each other. The second query electrode comprises a pair of electrodes 252 located on the cartridge channel 22 and electrically isolated from the cartridge channel 22 by an insulating material. The second query electrodes 252 are located on opposite sides of the knife channel 29 from each other. The first query electrodes 251 are directly opposed from corresponding second query electrodes 252 at the side periphery of the instrument so that the monitored impedance is based on tissue at the periphery, which is typically heated as tissue coagulation progresses from the middle of the instrument.

Although three different specific electrode configurations are illustrated in FIGS. 16, 18 and 19, it should be appreciated that numerous locations of query and therapeutic electrodes and wiring schemes are possible according to this invention, depending on, among other things, the location or stage of treatment at which tissue monitoring is desired. Additionally, one or more query electrodes may share a conductive path to the generator(s) with one or more treatment electrodes.

Figure 20A:
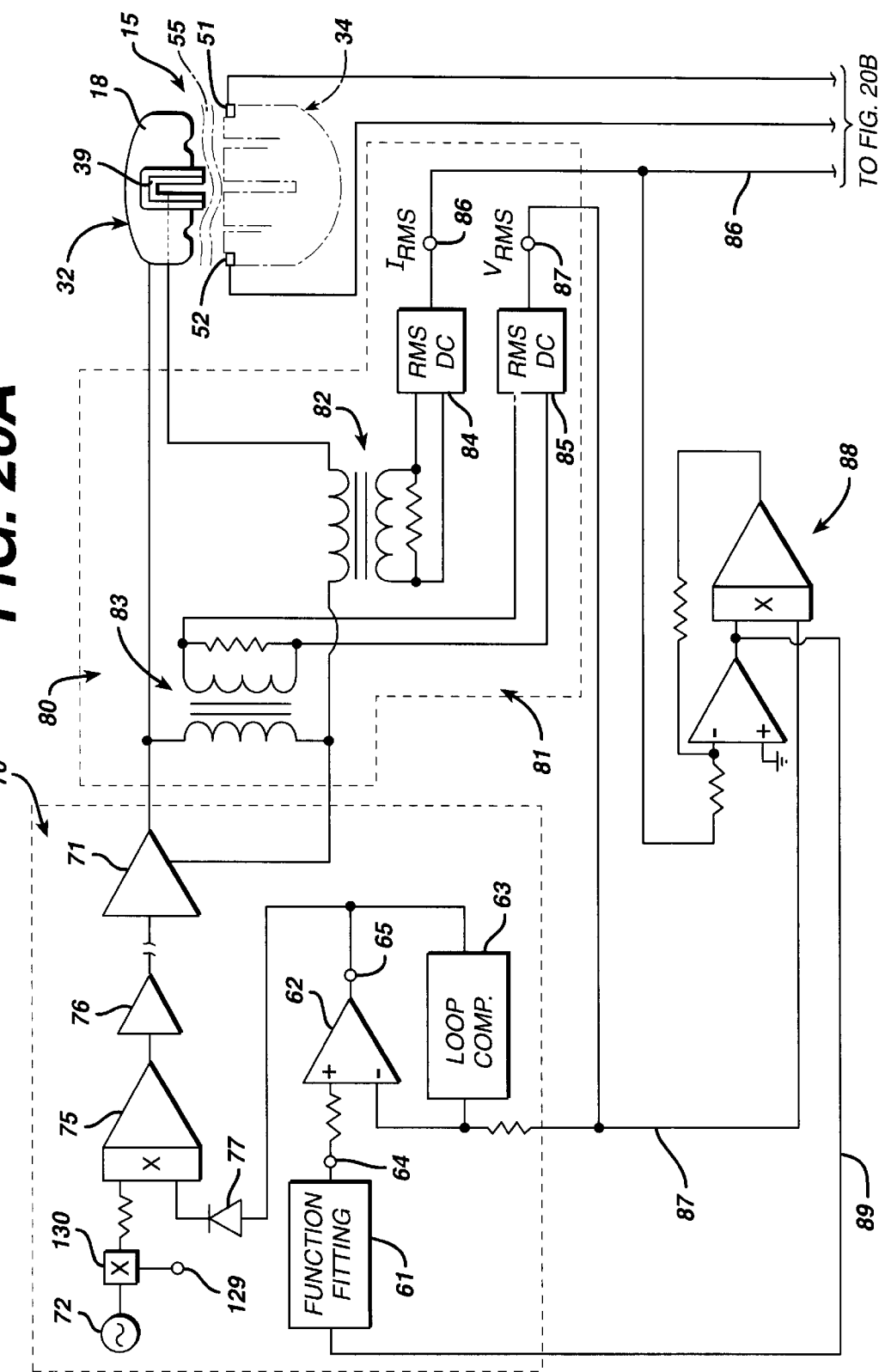
FIG. 20(a–b) is a schematic block diagram of an analog embodiment of the controller for use in the apparatus of FIG. 1.
Figure 20B:
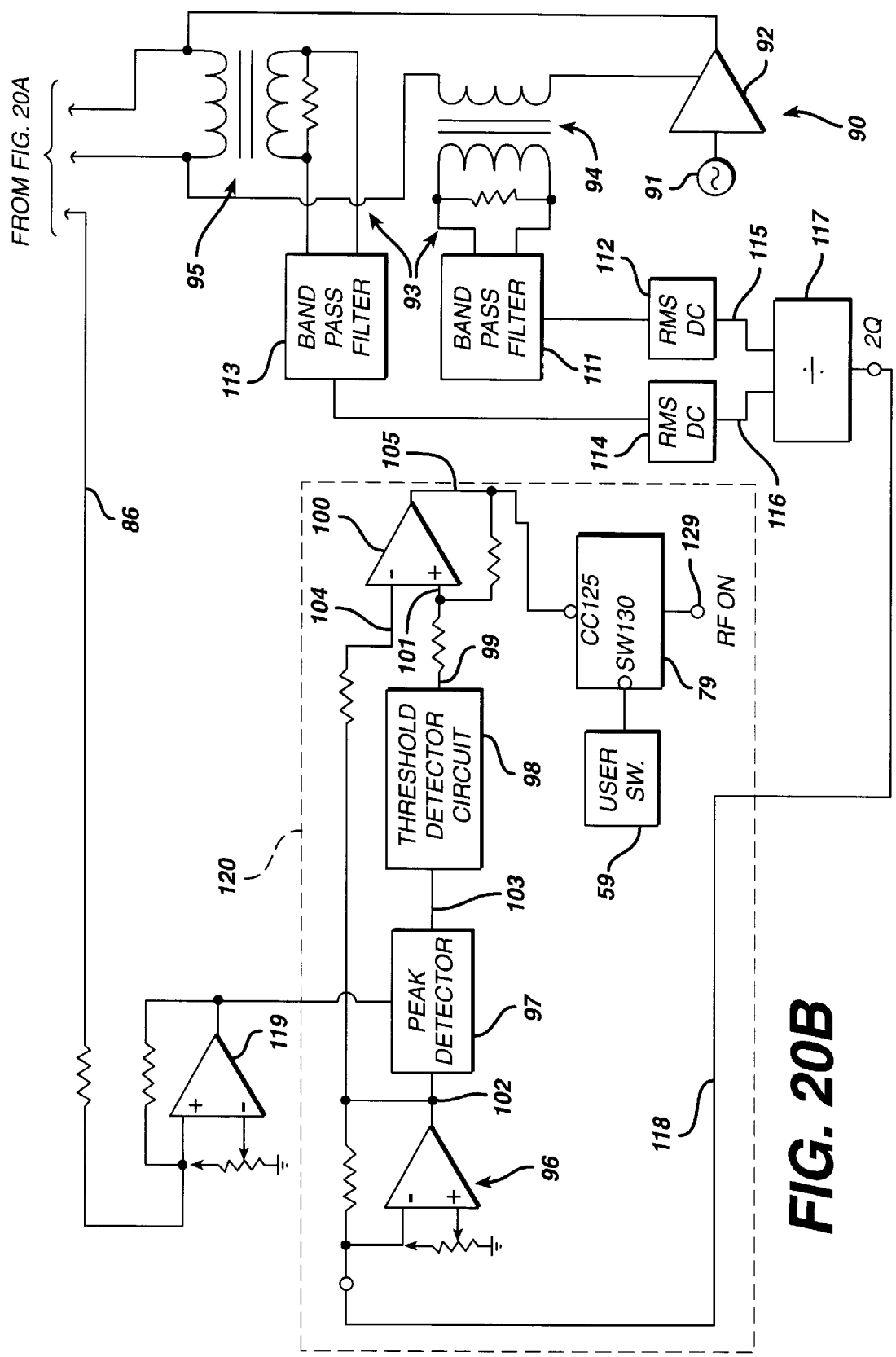

Referring now to FIG. 20 there is illustrated a schematic block diagram of an analog embodiment of the impedance monitoring device of the present invention. The impedance monitoring device determines when coagulation is complete.

The instrument 10 is positioned to engage tissue to be treated. Then, when appropriately positioned, RF energy is supplied to the tissue.

A first generator 70 supplies RF energy to the tissue engaged by the end effector 15 of the instrument 10 through therapeutic electrodes 39, 18. Preferably, 30 to 200 volts RMS at a fundamental frequency of about 300 Khz to 3 Mhz of a sinusoidal waveform, and a current of about 0.1 to 4.0 amps is supplied through the therapeutic electrodes 18, 39. A second generator 90 supplies electrical energy to the query electrodes 51, 52 at a different fundamental frequency within the frequency range above and preferably of a voltage of 2 volts or less and current of about 1 mA–100 mA.

The first generator 70 and second generator 90 are turned on by a user operated switch 59 located on housing 16. Alternatively, the second generator 90 may be switched on independently from the therapeutic signal.

The user operated switch 59 provides a signal to RF control input 130 of the controller 79, to turn on the therapeutic energy signal. The output 129 of the controller is coupled to an analog switch 130. When output 129 provides an "RF on" signal to the switch 130, an oscillator 72, coupled to an analog multiplier 75 through the switch 130, supplies a voltage of a known frequency to the analog multiplier 75. The output of the analog multiplier 75 is coupled to a driver 76 which is coupled to the input of an RF amplifier 71. A first amplified RF signal is supplied by the generator 70 to a circuit 80 which includes the first therapeutic electrode 39 and second therapeutic electrode (anvil 18) of the instrument 10, and the tissue 55 to be treated by the instrument 10. A second generator source 90 supplies a second electrical signal to first query electrode 51 and second query electrode 52. An oscillator 91 supplies a voltage of a different frequency than the therapeutic signal 72 to an RF amplifier 92 which provides a lower voltage signal to the query electrodes 51, 52.

An impedance sensor associated with the therapeutic electrodes includes a voltage and current sensor 81 which senses the current and voltage delivered to the tissue through the therapeutic electrodes 18, 39. The voltage and current sensor 81 includes a low impedance current transformer 82 in series with the generator 70 output at the therapeutic electrodes; and a high impedance voltage transformer 83 connected in parallel across the generator 70 output at the therapeutic electrodes. Preferably the current transformer 82 has, for example, a 1:20 winding ratio and a 50 ohm resistor in parallel with the secondary of the transformer. Preferably the voltage transformer 83 has, for example, a 20:1 winding ratio and a 1 K ohm resistor in parallel with the secondary of the transformer.

The output of the current transformer 82 is coupled to an RMS converter 84. The RMS converter 84 converts the sensed current to a DC signal to provide output 86, representative of the current RMS flowing between therapeutic electrodes 18, 39, $I_{TRMS}$. The output of the voltage transformer 83 is coupled to an RMS converter 85. The RMS converter 85 converts the voltage signal into an DC signal and provide output 87, representative of the voltage RMS between therapeutic electrodes 18, 39, $V_{TRMS}$. It should be noted here that provided the query signal had a significantly lower voltage than the tissue therapeutic signal, it would not be necessary to filter out the query signal when determining $V_{TRMS}$ and $I_{TRMS}$.

The measured impedance at the therapeutic electrodes, $Z_T$, is then calculated from the measured $I_{TRMS}$ and $V_{TRMS}$. The outputs 87, 86 of $V_{TRMS}$ and $I_{TRMS}$ are supplied to an analog divider 88 which divides the $V_{TRMS}$ by the $I_{TRMS}$ to provide an output signal 89 representative of the measured impedance, $Z_T$.

A preferred embodiment provides a control device which controls the generator energy output based on load impedance. In this embodiment, the impedance at the therapeutic electrodes, i.e., the tissue, is preferably used. However, the impedance at the query electrodes may be used to control generator output in an alternative embodiment. Either a measured impedance at the therapeutic electrodes measured by a current, or voltage sensing circuit (not shown) may be used or alternatively impedance at the query electrodes may be used for this purpose. The impedance at either the therapeutic electrodes or the query electrodes is used to determine a preferred energy level, e.g., voltage, current or power level, based on a specific system load curve for a generator, instrument and/or application. The control device then compares the actual energy level for the measured impedance with the desired energy level and adjusts the generator output according to the difference between the two, i.e., preferably to minimize the difference between the two.

The specific load curve in such a control device preferably reflects the voltage, current or power for a range of impedance that will optimize performance of the instrument. The load curve requirements may have various forms, for example, it may be continuous or may be stepped. The load curve may vary for a particular instrument in use with a generator, or for a particular electrosurgical application of the generator. For example, in a one embodiment using an instrument such as described herein, three impedance ranges have been identified at which different energy requirements exist: Initially tissue impedance is in a lower range, e.g., approximately 20 to 100 ohms. In the lower ranges, more current is required to provide enough power to initiate tissue coagulation. A second, mid-range of impedances, e.g., approximately 100 to 500 ohms, requires enough power to maintain the coagulation process. A third range of higher impedances typically occurring towards completion of coagulation, e.g., approximately 500 ohms and above, requires the voltage be limited to prevent sparking and tissue sticking. Thus the system load curve in this embodiment would reflect both the inherent characteristics of the generator and voltage output at which optimum power is delivered for a particular impedance, as well as the specific power requirements for a predetermined instrument and application.

The generator 70 includes a servo loop control device. The impedance signal 89 and the voltage $V_{TRMS}$ signal 87 are fed back to the generator 70 through a control device which comprises a function fitting device 61 and an error amplifier 62. The control device causes the generator 70 to produce voltages within a desired range based on a load impedance fit to a specific load curve.

The impedance 89 is fed to a function fitting device 61. The output 64 of the function fitting device 61 represents a desired voltage based on the input impedance 89. This desired voltage function is the voltage required for the generator 70 to produce a particular, pre-determined load curve. Desired voltage output 64 along with actual voltage is fed into an error amplifier 62. The output 65 of the error amplifier 62 represents an error voltage which is fed into an analog multiplier 75 through a diode 77.

Alternatively, current, power or another energy parameter may be used to control the output of the energy source or generator 70. A signal corresponding to impedance of the target is input into the function fitting device which provides a desired current, power or other energy parameter output, which is then compared to the measured or calculated current, power or other energy parameter.

The diode 77 ensures first quadrant operation of the analog multiplier 75. The analog multiplier 75 functions as an amplitude modulator of oscillator 72 such that large error voltages at output 65 result in large outputs from RF amplifier 71. And small error voltages of output 65 result in smaller RF output from RF amplifier 71. Thus, generator 70 acts as a closed-loop servo system based on voltage such that a desired load curve is obtained. The loop compensation device 63 acts to stabilize the servo loop. If an electrical parameter other than voltage is used, the form fitting function preferably outputs a signal reflecting the difference in the alternative energy parameter.

In an alternative embodiment (not shown) the impedance or other energy parameters related to the energy delivered to the query electrodes may be used to control the generator through the servo loop.

The generator 90 delivers the query signal to the query electrodes 51, 52. This signal may be turned on and left on independently of the therapeutic signal. Since the query signal is of a low voltage and will not effect tissue treatment the query signal may stay on. An impedance sensor associated with the query electrodes 51, 52 includes a voltage and current sensor 93 which senses the current and voltage delivered to the tissue through the query electrodes 51, 52. The sensor 93 includes a low impedance current transformer 94 in series with the generator 90 and a high impedance voltage transformer 95 connected in parallel across the generator 90 output to the query electrodes.

The output of the current transformer 94 is coupled to a band pass filter 111 arranged to pass frequencies at or around that of the query signal while filtering out frequencies at or around that of the therapeutic signal. The output of the band pass filter 111 is coupled to an RMS Converter 112. The RMS Converter 112 converts the sensed current to a DC signal to provide output 115 representative of the current RMS flowing between two query electrodes 51, 52, $I_{QRMS}$. The output of the voltage transformer 95 is coupled to a band pass filter 1 13 arranged to pass frequencies at or around the frequency of the query signal frequency while filtering out frequencies at or around that of the therapeutic signal frequency. The output of band pass filter 113 is coupled to an RMS converter 114. The RMS converter 114 converts the sensed voltage to a DC signal to provide output 116 representative of voltage RMS between the query electrodes 51, 52, $V_{QRMS}$.

The outputs 115, 116 are supplied to an analog divider 117 similar to analog divider 88. The analog divider 117 divides the $V_{QRMS}$ by the $I_{QRMS}$ to provide output signal 118 representative of the measured impedance $Z_Q$ at the query electrodes 51, 52.

In order for the coagulation complete detection to begin using the query electrodes, 51, 52 a minimum amount of current must be delivered to the therapeutic electrodes 18, 39. The $I_{TRMS}$ output 86 is input to a comparator 119 the output of which enables the peak detector 97 of the coagulation complete circuit 120.

A current above a minimum delivered to the therapeutic electrodes starts the coagulation complete circuit as described below. From the $I_{QRMS}$, $V_{QRMS}$ and measured impedance, $Z_Q$, the impedance sensing device determines whether coagulation is complete.

A coagulation complete condition is determined as follows: First, $Z_{min}$ is determined. Then, a target impedance at which coagulation is complete, $Z_{target}$, is calculated as a function of the minimum impedance. The initial impedance, $Z_{min}$, $Z_{target}$, slope of the impedance curve, and time to complete may vary for a given application and/or instrument, but tend to correlate to a function of minimum impedance. Depending on the instrument used and/or the actual desired result, the actual function of minimum impedance may vary. In this particular embodiment $f(Z_{min})$ is linear: $f(Z_{min})=0.2Z_{min}+500$. This function is bound, i.e., where $Z_{min}$ is >560 ohms, then $Z_{target}$ is $Z_{min}+50$ ohms. $f(Z_{min})$ may be a different function. It may be continuous, non-continuous, linear, non-linear, a piecewise approximation and/or in the form of a look-up table. $f(Z_{min})$ may also be bound at different values.

The impedance signal 118 is used to determine tissue coagulation as follows: First, a determination is made whether the measured $Z_Q$ is a minimum impedance, $Z_{min}$.

The $Z_Q$ impedance signal 118 is inverted and offset by a gain offset inverter 96. The output of the gain offset inverter 96 is in turn is coupled to a peak detector 97. The output 102 of the gain offset inverter is representative of an inverted and offset measured $Z_Q$, i.e., $(-Z_Q+k)$. $Z_{min}$ will now be represented by the highest offset value of $(-Z_Q+k)$ encountered.

The peak detector 97 is enabled by output of comparator 119 when a minimum threshold current is delivered through therapeutic electrodes 39, 18. The peak detector 97 thus detects and holds the highest value of the inverted and offset measured impedance, $Z_Q$, which is representative of $Z_{min}$. When $Z_{min}$ has occurred, the output 103 of the peak detector 97 is representative of $(-Z_{min}+k)$.

When the $Z_{min}$ has been determined, function of the $Z_{min}$, $(f(Z_{min}))$ is calculated to provide a impedance, $Z_{target}$, at which treatment (coagulation) is completed. The output 103 of the peak detector 97 is coupled to a threshold determining circuit 98 which calculates the $f(Z_{min})$ to determine the $Z_{target}$. The output 99 of the threshold determining circuit is representative of $Z_{target}$ when the measured impedance is equal to $Z_{min}$.

A continuous comparison is made between Z and $f(Z_{min})$. It should be noted here that $f(Z_{min})$ is continuously calculated as $f(Z)$ until a $Z_{min}$ is detected. The comparison is continuously made between $Z_Q$ and $f(Z_Q)$) until $Z_{min}$ is determined. This does not have a significant consequence, however, because it is anticipated that $f(Z_Q)$) will be larger than $Z_Q$ during tissue treatment and a premature coagulation complete signal therefore will not occur.

If measured $Z_Q$ is less than or equal to the $Z_{target}$ then RF energy is continued to be supplied and steps described above are carried out until or a coagulate complete signal is generated and received. If the measured $Z_Q$ is greater than or is equal to "$Z_{target}$" then a signal is provided to the controller that coagulation has been completed. Again it is noted that in this embodiment, $Z_Q$ has been inverted and shifted in order to accommodate $Z_{min}$ determination via the peak detector 97. The impedance values referred to in this paragraph are the actual impedance values.

The output 99, $Z_{target}$, of the threshold determining circuit 98 is coupled to the positive input 101 of a comparator OP amp 100. The output 102 of the gain offset inverter 96 is coupled to the negative input 104 of the comparator 100. The comparator 100 compares the $-Z_Q+k$ representative value which is input to the negative input 104 of the comparator 100, to the $Z_{target}$ representative value which is calculated as a function of $-Z_{min}+k$. If $-Z_Q+k$ is less than or equal to the $Z_{target}$, the comparator output 105 will be positive. That is, if the measured $Z_Q$ is greater than $f(Z_{min})$, a coagulation complete signal will appear at the output 105 of the comparator 100.

The signal at the output 105 is provided to the controller 79 indicating whether or not a coagulation complete condition exists. Upon the existence of a coagulation complete condition, the RF energy is automatically turned off by the controller.

The controller 79 has the following logic:

TABLE 1

| Switch (130) | CC (125) | RF ON (129) |
|---|---|---|
| 0 | 0 | 0 |
| 0 | 1 | 0 |
| 1 | 1 | 1 |
| 1 | 1 | 0 |

In operation, the end effector 15 of the instrument 10 is located at a tissue site where tissue is to be treated. The jaw members 32, 34 are opened and tissue is then placed between the interfacing inner surfaces 35, 33 respectively of jaw members 32, 34. The clamping trigger 12 is squeezed to cause the jaw members 32, 34 to close to locate and compress tissue between the opposing surfaces 33, 35. When the tissue has been appropriately situated between the jaw members 32, 34, a user may apply RF energy from the generators 70, 90 using a user activated switch 59.

The electrode bars 27, 28 and the insulating material 31, which together form the ridge 56, compress the tissue against the inner surface 35 of jaw member 34. Current flows through the compressed tissue between the first electrode 39, i.e. the bars 27, 28 and the electrically opposite electrode, i.e., the anvil 18. Current of a different frequency flows between first and second query electrodes 51, 52.

The impedance is measured by the query electrodes 51, 52, as described above until a coagulation complete condition has been determined and RF energy to the therapeutic electrodes is turned off.

If the coagulation complete status is indicated, the firing trigger 14 may be actuated to advance cutting element 1 1 through knife channels 26, 29 to cut engaged tissue between the bars 27, 28 where the tissue has been cauterized. Simultaneously, the firing trigger 14 advances the wedge 113 through track 25 to advance drivers 24 to fire staples 17 through tissue and into pockets 36 of the anvil 18. Thus, the cut line is medial to the coagulation lines formed by the bar electrodes 27, 28 and staples 17 are applied into longitudinally single rows on each side of the cutting element 11 as the cutting element 11 cuts the tissue.

In one embodiment, the cartridge provides multifire stapling capabilities by having single rows of staples, as opposed to the convention double row of staples of the cartridges in the laparoscopic stapling and cutting devices presently in use. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. The device of the present may however, if desired, include double, triple, etc., staple rows. Also, in a further embodiment, no staples are required and the electrical coagulation lines provide the necessary hemostasis or tissue welding effect.

The above described preferred embodiment may be incorporated into a circular stapler. Operation of circular staplers is known in the art and is described, for example in U.S. Pat. No. 5,104,025 incorporated herein by reference. A variation of the embodiments described herein may provide a tissue welding and cauterizing cutting device similar to an intraluminal stapler. In this embodiment, a device similar to that described in parent application Ser. No. 08/095,797 filed on Jul. 22, 1993 is provided. The electrodes are formed in two concentric circle electrodes separated by an insulator. The electrodes are located radially inward or radially outward of the insulator which forms the compression ridge and on either of the interfacing surfaces. The electrodes of the stapling embodiment of the circular cutting device may be located on either the stapler cartridge or the anvil.

The invention described and the specific details and the manner in which it may be carried out having been exemplified it will be readily apparent to those skilled in the art that innumerable variations, modifications, and extensions of the basic principles involved may be made without departing from the spirit and scope of the present invention. The impedance feedback system as described above is used to indicate when sufficient cauterization has occurred. When coagulation is complete, a signal may be provided by a controller to a user, or a controller may automatically turn off the RF energy. Other signals may be provided to an instrument user as well. For example a tone corresponding to the measured impedance may be provided to a user to audibly monitor the change in impedance.

It is also intended that this device and/or method be used with numerous types of electrosurgical instruments including monopolar, bipolar and multipolar configurations. A number of different impedance feedback systems may also be used to determine coagulation complete or another tissue characteristic or status. The location of the query electrodes may vary as well. The query electrodes may be energized continuously through treatment, periodically or at specific times either predetermined or user initiated. The impedance feedback system may be included in part or in whole with the actual instrument, as a separate unit and/or with the energy source or generator.

What is claimed is:

1. An electrosurgical device for treating tissue during a surgical procedure, said device comprising:
   a surgical instrument having a tissue treating portion including an end effector adapted to engage tissue to be treated, said end effector comprising first and second opposing interfacing surfaces adapted to engage tissue to be treated therebetween;
   electrically isolated first and second therapeutic poles comprised of tissue contacting first and second therapeutic electrodes adapted to receive electrosurgical energy from an energy source and capable of conducting electrical energy therebetween, at least one of said first and second therapeutic electrodes being positioned on at least one of said first and second interfacing surfaces; and
   electrically isolated first and second query poles comprised of tissue contacting first and second query electrodes adapted to receive electrosurgical energy from an energy source and capable of conducting electrical energy therebetween, said first query electrode being positioned on one of said first and second interfacing surfaces and said second query electrode being positioned on one of said first and second interfacing surfaces.

2. The electrosurgical device of claim 1 wherein said electrical parameter comprises a phase difference between voltage and current.

3. An electrosurgical device having an end effector, wherein said end effector comprises:
   first and second opposing interfacing surfaces, said interfacing surfaces capable of engaging tissue therebetween, and end effector capable of receiving electrosurgical energy therein,
   electrically isolated first and second therapeutic poles comprised of first and second electrically opposite therapeutic electrodes capable of conducting electrosurgical energy therethrough;
   electrically isolated first and second sensing poles comprised of first and second electrically opposite query electrodes capable of conducting electrosurgical energy therebetween;
   wherein said first therapeutic electrode is located on at least one of said first and second interfacing surfaces and said second therapeutic electrode is located on said end effector so that electrosurgical energy may be communicated between said therapeutic poles through the tissue engaged by said interfacing surfaces to electrosurgically treat the tissue; and
   wherein said first query electrode is located on at least one of said first and second interfacing surfaces and said second query electrode is located on said end effector so that sensing electrosurgical energy may be communicated between said sensing poles to measure an electrical parameter of said tissue between said sensing poles.

4. The electrosurgical device of claim 3 wherein each of said therapeutic electrodes is located on at least one of said first and second interfacing surfaces.

5. The electrosurgical device of claim 3 wherein each of said first and second query electrodes is located on at least one of said first and second interfacing surfaces.

6. The electrosurgical device of claim 3 wherein a portion of at least one of said first and second interfacing surfaces comprises a ridge forming a tissue compression zone between said first and second interfacing surfaces, said end effector further comprising a plane bisecting said interfacing surfaces and said ridge;
   wherein said query electrodes are located on opposite lateral sides of said compression ridge with respect to said plane.

7. The electrosurgical device of claim 6 wherein therapeutic electrodes are arranged to provide electrosurgical tissue treatment in the compression zone when current flows between said first and second therapeutic poles.

8. The electrosurgical device of claim 3 wherein one of said first and second therapeutic poles is the same electrical potential as one of said first and second sensing poles.

9. The electrosurgical device of claim 3 further comprising a cutting element associated with said end effector, said cutting element adapted to divide tissue engaged by said end effector, through a cutting line.

10. The electrosurgical device of claim 9 wherein said query electrodes are located on opposing sides of said cutting line.

11. the electrosurgical device of claim 3 wherein said first query electrode is arranged on a periphery of said at least one interfacing surface so as to be adapted to measure the impedance of the engaged tissue at the periphery.

12. The electrosurgical device of claim 3 wherein said electrical parameter comprises current delivered to said tissue.

13. The electrosurgical device of claim 3 wherein said electrical parameter comprises voltage delivered to said tissue.

14. The electrosurgical device of claim 3 wherein said electrical parameter comprises tissue impedance.

15. The electrosurgical device of claim 3 wherein said electrical parameter comprises voltage and current delivered to tissue from which impedance of tissue between said query electrodes may be determined.

16. An electrosurgical device having an end effector, wherein said end effector comprises:
   first and second opposing interfacing surfaces, said interfacing surfaces capable of engaging tissue therebetween, and end effector capable of receiving electrosurgical energy therein,
   electrically isolated first and second therapeutic poles comprised of first and second electrically opposite therapeutic electrodes capable of conducting electrosurgical energy therethrough;

electrically isolated first and second sensing poles comprised of first and second electrically opposite query electrodes capable of conducting electrosurgical energy therebetween;

wherein said first therapeutic electrode is located on at least one of said first and second interfacing surfaces and said second therapeutic electrode is located on said end effector so that electrosurgical energy may be communicated between said therapeutic poles through the tissue engaged by said interfacing surfaces to electrosurgically treat the tissue; and wherein said first query electrode is located on at least one of said first and second interfacing surfaces and said second query electrode is located on said end effector so that sensing electrosurgical energy may be communicated between said sensing poles to measure an electrical parameter of said sensing electrosurgical energy delivered between said sensing poles.

17. The electrosurgical device of claim 16 wherein each of said therapeutic electrodes is located on at least one of said first and second interfacing surfaces.

18. The electrosurgical device of claim 16 wherein each of said first and second query electrodes is located on at least one of said first and second interfacing surfaces.

19. An electrosurgical method comprising:
providing an electrosurgical device having an end effector, wherein said end effector comprises:
first and second opposing interfacing surfaces, said interfacing surfaces capable of engaging tissue therebetween, and end effector capable of receiving electrosurgical energy therein, electrically isolated first and second therapeutic poles comprised of electrically opposite therapeutic electrodes capable of conducting electrosurgical energy therethrough; and
electrically isolated first and second sensing poles comprised of electrically opposite query electrodes capable of conducting electrosurgical energy therebetween;
wherein each of said therapeutic electrodes and each of said first and second query electrodes is located on a said interfacing surface;
engaging tissue between said surfaces;
delivering therapeutic electrosurgical energy to said tissue between said therapeutic electrodes;
delivering sensing electrosurgical energy to said tissue between said sensing electrodes;
measuring an electrical parameter of said sensing electrosurgical energy;
determining when a desired tissue effect has occurred; and
providing a signal indicating said tissue effect.

20. The method of claim 19 wherein said tissue effect is a coagulation complete condition.

21. The method of claim 19 wherein said electrical parameter is tissue impedance.

22. The electrosurgical method of claim 19 wherein the step of delivering sensing electrosurgical energy occurs at the same time as the step of delivering therapeutic electrosurgical energy.

23. The electrosurgical method of claim 19 wherein the step of delivering sensing electrosurgical energy occurs prior to the step of delivering therapeutic electrosurgical energy.

24. The electrosurgical method of claim 19 wherein the step of delivering sensing electrosurgical energy occurs after the step of delivering therapeutic electrosurgical energy.

25. An electrosurgical device for treating tissue during a surgical procedure, said device comprising;

a surgical instrument having a tissue treating portion including an end effector adapted to engage tissue to be treated;

electrically isolated first and second therapeutic poles comprised of tissue contacting first and second therapeutic electrodes adapted to receive electrosurgical energy from an energy source and capable of conducting electrical energy therebetween, fat least said first therapeutic electrode being positioned on said tissue treating portion of said instrument and said second therapeutic electrode being positioned on said end effector;

electrically isolated first and second query poles comprised of tissue contacting first and second query electrodes adapted to receive electrosurgical energy from an energy source and capable of conducting electrical energy therebetween, of said first query electrodes being positioned on said tissue treating portion of said instrument and said second query electrode being positioned on said end effector;

a tissue treatment status determining device including electrical parameter measuring circuitry coupled to said query electrodes for measuring an electrical parameter of tissue engaged by said end effector, said tissue treatment status determining device adapted to provide an energy control signal for controlling electrosurgical energy supplied to said therapeutic electrodes.

26. The electrosurgical device of claim 25 further comprising:
an energy source arranged to supply electrosurgical energy to said therapeutic electrodes, wherein said energy source is responsive to said control signal to supply said energy to said therapeutic electrodes.

27. The electrosurgical device of claim 25 wherein said electrical parameter measuring circuitry includes:
a first device for determining the minimum impedance value;
a target determining device coupled to said first device, for determining the target impedance value as a function of said minimum impedance value; and
a first comparison device for comparing measured impedance values to said target impedance value and generating a signal indicating whether said measured impedance value exceeds said target impedance value.

28. The electrosurgical device of claim 25 wherein said end effector includes first and second elements movable relative to each other for engaging tissue therebetween, wherein said first therapeutic electrode is located on at least one of said first and second elements.

29. The electrosurgical device of claim 28 wherein said second therapeutic electrode is located on at least one of said first and second elements.

30. The electrosurgical device of claim 29 wherein said first and second query electrodes are each located on either one or both of said first and second elements; and wherein said electrical parameter measuring circuitry is adapted to measure an electrical parameter of the tissue between said first and second query electrodes and engaged by said first and second elements.

31. The electrosurgical device of claim 30, wherein each of said first therapeutic electrodes is offset from each of said second therapeutic electrodes with respect to said interfacing surfaces.

32. The electrosurgical device of claim 28, wherein:
said first and second elements comprise first and second interfacing surfaces for engaging tissue to be electrosurgically treated;

wherein said first therapeutic pole is comprised of one or more first therapeutic electrodes located on at least one of said first and second interfacing surfaces; and wherein said second therapeutic pole is comprised of one or more second therapeutic electrodes located on at least one of said first and second interfacing surfaces.

33. The electrosurgical device of claim 32, wherein each of said one or more first therapeutic electrodes is offset from each of said one or more second therapeutic electrodes with respect to said interfacing surfaces.

34. The electrosurgical device of claim 25 wherein said electrical parameter determining circuitry comprises impedance measuring circuitry for measuring impedance of tissue engaged by said end effector.

35. The electrosurgical device of claim 34 wherein said impedance measuring circuitry is adapted to:

determine a minimum impedance value of tissue between the query electrodes as said tissue between the therapeutic electrodes is treated with therapeutic energy by the treatment electrodes;

determine a target impedance value at which a desired tissue status is attained, said target value being a function of said minimum impedance value; and compare measured impedance values of tissue between the query electrodes to the target impedance value and adjust said control signal when said measured impedance value exceeds said target impedance value.

36. The electrosurgical device of claim 25 wherein said tissue status determining device comprises a tissue coagulation status determining device for determining a degree of coagulation of tissue being treated by said therapeutic electrodes.

37. A method of electrosurgically treating tissue, said method comprising the steps of:

providing an electrosurgical instrument including electrically different query electrodes; electrically different therapeutic electrodes; and an end effector comprising one or more of said tissue treating electrodes and one or more of said query electrodes;

applying sensing electrosurgical energy through said one or more query electrodes to tissue to be electrosurgically treated;

measuring an electrical parameter of the tissue between said query electrodes;

generating a signal representative of the measured electrical parameter of tissue between said query electrodes;

determining a therapeutic target electrical parameter value from said measured electrical parameter;

comparing subsequent measured electrical parameters to said target value;

generating a control signal to control the electrosurgical energy to said electrosurgical instrument in response to said measured electrical parameter reaching said target value; and controlling the energy applied to the tissue through said one or more therapeutic electrodes in response to said control signal.

38. A method of electrosurgically treating tissue, said method comprising the steps of:

providing an electrosurgical instrument including electrically different query electrodes; electrically different therapeutic electrodes; and an end effector comprising one or more of said tissue treating electrodes and one or more of said query electrodes;

applying sensing electrosurgical energy through said one or more query electrodes to tissue to be electrosurgically treated;

measuring the impedance of the tissue between said query electrodes;

generating an impedance signal representative of the measured impedance value of tissue between said query electrodes;

determining a representative minimum impedance value from said impedance signal;

determining a representative target impedance value as a function of said minimum impedance value;

comparing subsequent impedance signals to said target impedance value;

generating a control signal to control the electrosurgical energy to said electrosurgical instrument in response to said measured impedance value reaching said target impedance value; and controlling the energy applied to the tissue through said one or more therapeutic electrodes in response to said control signal.

39. The method of claim 38 further comprising;

providing tissue contacting opposing surfaces included with said end effector wherein said surfaces engaging tissue to be treated between said surfaces are moveable to engage tissue to be treated therebetween; and wherein said query electrodes and said one or more therapeutic electrodes are each positioned on either one or both of said surfaces.

40. A method of electrosurgically treating tissue comprising the steps of:

providing an electrosurgical instrument having an end effector comprising first and second tissue engaging surfaces, one of said first and second tissue engaging surfaces including thereon a first tissue contacting therapeutic electrode electrically connected to a first pole of an electrosurgical therapeutic system, and one of said first and second tissue engaging surfaces containing thereon a second tissue contacting therapeutic electrode electrically connected to a second pole of the therapeutic system; one of said first and second tissue engaging surfaces including thereon a first query electrode electrically connected to a first pole of an impedance sensing system and one of said first and second tissue engaging surfaces including thereon a second query electrode electrically connected to a second pole of said impedance sensing system;

engaging tissue to be treated between the first and second tissue engaging surfaces;

selectively controlling electrosurgical energy supplied to the first and second tissue contacting therapeutic electrodes for treating tissue positioned therebetween;

measuring the impedance of the treated tissue between the first and second query electrodes with said first and second query electrodes;

setting a threshold impedance value at which tissue treatment is complete;

comparing measured impedance values to the threshold impedance value; and controlling or switching off the electrosurgical energy coupled to the first and second therapeutic electrodes upon the condition of the measured impedance value reaching or exceeding the threshold impedance value.

41. An electrosurgical impedance feedback control device, said device comprising:

an energy control signal generating device for generating a control signal to control electrosurgical energy supplied from an energy source to one or more therapeutic electrodes positioned on a tissue treating portion of a surgical instrument;

impedance measurement circuitry adapted to be coupled to at least one tissue contacting query electrode positioned on the tissue treating portion of the surgical instrument and to an energy source arranged to supply therapeutic electrosurgical energy to the one or more therapeutic electrodes positioned on the tissue treating portion of the surgical instrument, wherein said impedance measurement circuitry is adapted to measure the impedance of tissue engaged by the tissue treating portion of the surgical instrument;

wherein said impedance measuring circuitry comprises:
 a first device for determining a minimum impedance value;
 a target determining device coupled to said first device, for determining the target impedance value as a function of said minimum impedance value; and
 a first comparison device for comparing measured impedance values to said target impedance value and generating a signal indicating whether said measured impedance value exceeds said target impedance value.

* * * * *